（12） United States Patent
Svendsen et al.

US009487769B2

(10) Patent No.: US 9,487,769 B2
(45) Date of Patent: *Nov. 8, 2016

(54) ALPHA-AMYLASE MUTANTS

(71) Applicant: NOVOZYMES A/S, Bagsvaerd (DK)

(72) Inventors: Allan Svendsen, Bagsvaerd (DK);
Torben Vedel Borchert, Bagsvaerd (DK); Henrik Bisgaard-Frantzen, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/638,666

(22) Filed: Mar. 4, 2015

(65) Prior Publication Data

US 2015/0175986 A1    Jun. 25, 2015

Related U.S. Application Data

(60) Division of application No. 13/953,409, filed on Jul. 29, 2013, now Pat. No. 8,999,908, which is a division of application No. 13/557,313, filed on Jul. 25, 2012, now Pat. No. 8,513,175, which is a division of application No. 13/100,407, filed on May 4, 2011, now Pat. No. 8,263,382, which is a continuation of application No. 11/862,580, filed on Sep. 27, 2007, now Pat. No. 7,960,161, which is a division of application No. 10/980,759, filed on Nov. 3, 2004, now Pat. No. 7,625,737, which is a continuation of application No. 10/644,187, filed on Aug. 20, 2003, now abandoned, which is a division of application No. 10/186,042, filed on Jun. 28, 2002, now Pat. No. 6,642,044, which is a division of application No. 09/672,459, filed on Sep. 28, 2000, now Pat. No. 6,436,888, which is a continuation of application No. 09/182,859, filed on Oct. 29, 1998, now Pat. No. 6,143,708, which is a continuation of application No. PCT/DK97/00197, filed on Apr. 30, 1997.

(30) Foreign Application Priority Data

Apr. 30, 1996 (DK) .................................. 0515/96
Jun. 28, 1996 (DK) .................................. 0712/96
Jul. 11, 1996 (DK) .................................. 0775/96
Nov. 8, 1996 (DK) .................................. 1263/96

(51) Int. Cl.
C12N 9/28       (2006.01)
C11D 3/386      (2006.01)
C12P 19/14      (2006.01)
C12P 19/02      (2006.01)

(52) U.S. Cl.
CPC ............ C12N 9/2417 (2013.01); C11D 3/386 (2013.01); C12P 19/02 (2013.01); C12P 19/14 (2013.01)

(58) Field of Classification Search
CPC .............................. C12P 19/02; C12P 19/14
USPC ......................................................... 435/202
See application file for complete search history.

(56) References Cited

U.S. PATENT DOCUMENTS

| 5,731,280 | A |  | 3/1998 | Nielson et al. |
|---|---|---|---|---|
| 5,736,499 | A |  | 4/1998 | Mitchinson et al. |
| 5,824,532 | A |  | 10/1998 | Barnett et al. |
| 6,143,708 | A | * | 11/2000 | Svendsen ............... C11D 3/386 435/202 |
| 6,297,038 | B1 |  | 10/2001 | Bisgard-Frantzen |
| 6,410,295 | B1 |  | 6/2002 | Anderson et al. |
| 6,436,888 | B1 |  | 8/2002 | Svendsen et al. |
| 6,440,716 | B1 |  | 8/2002 | Svendsen et al. |
| 6,642,044 | B2 |  | 11/2003 | Svendsen et al. |
| 6,867,031 | B2 |  | 3/2005 | Bisgard-Frantzen |
| 6,887,986 | B1 |  | 5/2005 | Svendsen et al. |
| 7,625,737 | B2 | * | 12/2009 | Svendsen ............... C11D 3/386 435/202 |
| 7,713,723 | B1 |  | 5/2010 | Thisted et al. |
| 2002/0155574 | A1 |  | 10/2002 | Thisted et al. |

FOREIGN PATENT DOCUMENTS

| WO | 91/00353 A2 | 6/1990 |
|---|---|---|
| WO | 90/11352 A1 | 10/1990 |
| WO | 95/10603 A1 | 4/1995 |
| WO | 95/35382 A2 | 5/1995 |
| WO | 95/26397 A1 | 10/1995 |
| WO | 96/23874 A1 | 8/1996 |

OTHER PUBLICATIONS

Boel et al., 1990, Biochemistry, vol. 29, No. 26, pp. 6244-6249.
Declerck et al., 1990, J. Biol. Chem. vol. 265, No. 26, pp. 15481-15488.
Holm et al., 1990, Protein Engineering, vol. 3, No. 3, pp. 181-191.
Kaneko et al., 1989, J. Gen. Microbiol., vol. 135, pp. 3447-3457, Sequence Alignment No. P30921.
Machius et al., 1995, J. Mol. Biol., vol. 246, No. 4, pp. 545-559.
Takkinen et al., 1980, J. Biochem., vol. 185, pp. 387-395, Sequence Alignment No. P00692.
Takkinen et al., 1983, J. Biol. Chem., vol. 258, pp. 1007-1013, Sequence Alignment No. A92389.

* cited by examiner

Primary Examiner — Tekchand Saidha
(74) Attorney, Agent, or Firm — Michael W. Krenicky

(57) ABSTRACT

The invention relates to a variant of a parent Termamyl-like alpha-amylase, which variant has alpha-amylase activity and exhibits an alteration in at least one of the following properties relative to the parent alpha-amylase: substrate specificity, substrate binding, substrate cleavage pattern, thermal stability, pH/activity profile, pH/stability profile, stability towards oxidation, $Ca^{2+}$ dependency and specific activity.

18 Claims, 9 Drawing Sheets

FIG. 1A

```
1
CAT CAT AAT GGA ACA AAT GGT ACT ATG CAA TAT TTC GAA TGG TAT TTG CCA AAT GAC
 H   H   N   G   T   N   G   T   M   Q   Y   F   E   W   Y   L   P   N   D

21
GGG AAT CAT TGG AAC AGG TTG AGG GAT GAC GCA GCT AAC TTA AAG AGT AAA GGG ATA ACA
 G   N   H   W   N   R   L   R   D   D   A   A   N   L   K   S   K   G   I   T

41
GCT GTA TGG ATC CCA CCT GCA TGG AAG GGG ACT TCC CAG AAT GAT GTA GGT TAT GGA GCC
 A   V   W   I   P   P   A   W   K   G   T   S   Q   N   D   V   G   Y   G   A

61
TAT GAT TTA TAT GAT CTT GGA GAG TTT AAC CAG AAG GGG ACG GTT CGT ACA AAA TAT GGA
 Y   D   L   Y   D   L   G   E   F   N   Q   K   G   T   V   R   T   K   Y   G

81
ACA CGC AAC CAG CTA CAG GCT GCG GTG ACC TCT TTA AAA AAT AAC GGC ATT CAG GTA TAT
 T   R   N   Q   L   Q   A   A   V   T   S   L   K   N   N   G   I   Q   V   Y
```

FIG.1B

```
101
GGT GAT GTC GTC ATG AAT CAT AAA GGT GGA GCA GAT GGT ACG GAA ATT GTA AAT GCG GTA
 G   D   V   V   M   N   H   K   G   G   A   D   G   T   E   I   V   N   A   V

121
GAA GTC AAT CGG AGC AAC CAG GAA ACC TCA GGA GAG TAT GCA ATA GAA GCG TGG
 E   V   N   R   S   N   Q   E   T   S   G   E   Y   A   I   E   A   W

141
ACA AAG TTT GAT TTT CCT GGA AGA GGA AAT AAC CAT TCC AGC TTT AAG TGG CGC TGG TAT
 T   K   F   D   F   P   G   R   G   N   N   H   S   S   F   K   W   R   W   Y

161
CAT TTT GAT GGG ACA GAT TGG GAT CAG TCA CGC CAG CTT CAA AAC AAA ATA TAT AAA TTC
 H   F   D   G   T   D   W   D   Q   S   R   Q   L   Q   N   K   I   Y   K   F

181
AGG GGA ACA GGC AAG GCC TGG GAC TGG GAA GTC GAT ACA GAG AAT GGC AAC TAT GAC TAT
 R   G   T   G   K   A   W   D   W   E   V   D   T   E   N   G   N   Y   D   Y
```

FIG.1C

```
201
CTT ATG TAT GCA GAC GTG GAT ATG GAT CAC CCA GAA GTA ATA CAT GAA CTT AGA AAC TGG
 L   M   Y   A   D   V   D   M   D   H   P   E   V   I   H   E   L   R   N   W

221
GGA GTG TGG TAT ACG AAT ACA CTG AAC CTT GAT GGA TTT ACA ATA GAT GCA GTG AAA CAT
 G   V   W   Y   T   N   T   L   N   L   D   G   F   T   I   D   A   V   K   H

241
ATA AAA TAT AGC TTT ACG AGA GAT TGG CTT ACA CAT GTG CGT AAC ACC ACA GGT AAA CCA
 I   K   Y   S   F   T   R   D   W   L   T   H   V   R   N   T   T   G   K   P

261
ATG TTT GCA GTG GCT GAG TTT TGG AAA AAT GAC CTT GGT GCA ATT GAA AAC TAT TTG AAT
 M   F   A   V   A   E   F   W   K   N   D   L   G   A   I   E   N   Y   L   N

291
AAA ACA AGT TGG AAT CAC TCG GTG TTT GAT GTT CCT CTC CAC TAT AAT TTG TAC AAT GCA
 K   T   S   W   N   H   S   V   F   D   V   P   L   H   Y   N   L   Y   N   A
```

FIG.1D

```
301 TCT AAT AGC GGT TAT GGT TAT GAT ATG AGA AAT ATT TTA AAT GGT TCT GTG GTG CAA AAA
    S   N   S   G   Y   G   Y   D   M   R   N   I   L   N   G   S   V   V   Q   K

321 CAT CCA ACA CAT GCC GTT ACT TTT GTT GAT AAC CAT GAT TCT CAG CCC GGG GAA GCA TTG
    H   P   T   H   A   V   T   F   V   D   N   H   D   S   Q   P   G   E   A   L

341 GAA TCC TTT GTT CAA CAA TGG TTT AAA CCA CTT GCA TAT GCA TTG GTT CTG ACA AGG GAA
    E   S   F   V   Q   Q   W   F   K   P   L   A   Y   A   L   V   L   T   R   E

361 CAA GGT TAT CCT TCC GTA TTT TAT GGG GAT TAC TAC GGT ATC CCA ACC CAT GGT GTT CCG
    Q   G   Y   P   S   V   F   Y   G   D   Y   Y   G   I   P   T   H   G   V   P

381 GCT ATG AAA TCT AAA ATA GAC CCT CTT CTG CAG GCA CGT CAA ACT TTT GCC TAT GGT ACG
    A   M   K   S   K   I   D   P   L   L   Q   A   R   Q   T   F   A   Y   G   T
```

FIG.1E

```
401
CAG CAT GAT TAC TTT GAT CAT CAT GAT ATT ATC GGT TGG ACA AGA GAG GGA AAT AGC TCC
 Q   H   D   Y   F   D   H   H   D   I   I   G   W   T   R   E   G   N   S   S

421
CAT CCA AAT TCA GGC CTT GCC ACC ATT ATG TCA GAT GGT CCA GGT AAC AAA TGG ATG
 H   P   N   S   G   L   A   T   I   M   S   D   G   P   G   N   K   W   M

441
TAT GTG GGG AAA AAT AAA GCG GGA CAA GTT TGG ACA GAT ATT ACC GGA AAT AGG ACA GGC
 Y   V   G   K   N   K   A   G   Q   V   W   R   D   I   T   G   N   R   T   G

261
ACC GTC ACA ATT AAT GCA GAC GGA TGG GGT AAT TTC TCT GTT AAT GGA GGG TCC GTT TCG
 T   V   T   I   N   A   D   G   W   G   N   F   S   V   N   G   G   S   V   S

481
GTT TGG GTG AAG CAA TAA
 V   W   V   K   Q   *
```

FIG. 2A

```
              10         20         30         40         50         60
              |          |          |          |          |          |
1  HHNGTNGTMMQYFEWYLPNDGNHWNRLRDDAANLKSKGITAVWIPPAWKGTSQNDVGYGA    60
3  -AAPFNGTMMQYFEWYLPDDGTLWTKVANEANNLSSLGITALWLPPAYKGTSRSDVGYGV    59
2  HHNGTNGTMMQYFEWHLPNDGNHWNRLRDDASNLRRGITAIWIPPAWKGTSQNDVGYGA    60
4  HHNGTNGTMMQYFEWYLPNDGNHWNRLNSDASNLKSKGITAVWIPPAWKGASQNDVGYGA    60

70         80         90        100        110        120
              |          |          |          |          |          |
1  YDLYDLGEFNQKGTVRTKYGTRNQLQAAVTSLKNNGIQVYGDVVMNHKGGADGTEIVNAV   120
3  YDLYDLGEFNQKGTVRTKYGTKAQYLQAIQAAHAAGMQVYADVVFDHKGGADGTEWDAV    119
2  YDLYDLGEFNQKGTVRTKYGTRSQLESAIHALKVNGVQVYGDVVMNHKGGADATENVLAV   120
4  YDLYDLGEFNQKGTVRTKYGTRSQLQAAVTSLKNNGIQVYGDVVMNHKGGADATEMVRAV   120

130        140        150        160        170        180
              |          |          |          |          |          |
1  EVNRSNRPNQETSGEYAIEANTKFDFPGRGNNHSSFKWRWYHFDGTDWDQSRQLQNKIYKF   180
3  EVNPSDRNQEISGTYQIQANTKFDFPGRGNTYSSFKWRWYHFDGVDWDESRKLS-RIYKF   178
2  EVNPNNRNQEISGDYTIEAWTKFDFPGRGNTYSDFKWRWYHFDGVDWDQSRQFQNRIYKF   180
4  EVNPNNRNQEVTGEYTIEAWTRFDFPGRGNTHSSFKWRWYHFDGVDWDQSRRLNNRIYKF   180
```

FIG.2B

```
             190        200        210        220        230        240
              |          |          |          |          |          |
1  RGTGKAWDWEVDTENGNYDYLMYADVDMDHPEVIHELRNWGVWYTNTLNLDGFRIDAVKH  240
3  RGIGKAWDWEVDTENGNYDYLMYADLDMDHPEVVTELKNWGKWYVNTTNIDGFRLDAVKH  238
2  RGDGKAWDWEVDSENGNYDYLMYADVDMDHPEVVNELRRWGEWYTNTLNLDGFRIDAVKH  240
4  RGHGKAWDWEVDTENGNYDYLMYADIDMDHPEVVNELRNWGVWYTNTLGLDGFRIDAVKH  240

250        260        270        280        290        300
              |          |          |          |          |          |
1  IKYSFTRDWLTHVRNTTGKPMFAVAEFWKQDLGAIENYLNKTSWNHSAFDVPLHYNLYNA  300
3  IKFSFFPDWLSYVVRSQTGKPLFTVGEYWSYDINKLHNYITKTDGTMSLFDAPLHNKFYTA  298
2  IKYSFTRDWLTHVRNATGKEMFAVAEFWKQDLGAIENYLNKTNWNHSVFDVPLHYNLYNA  300
4  IKYSFTRDWINHVRSATGKNMFAVAEFWKQDLGAIENYLQKTNWNHSVFDVPLHYNLYNA  300

310        320        330        340        350        360
              |          |          |          |          |          |
1  SNSGGYYDMRNILNGSVVQKHPTHAVTFVDNHDSQPGEALESFVQQWFKPLAYALVLTRI  360
3  SKSGGAFDMRTLMTNTLMKDQPTLAVTFVDNHDTEPGQALQSWVDPWFKPLAYAFILTRQ  358
2  SNSGGNYDMAKLLNGTVVQKHPMHAVTFVDNHDSQPGESLESFVQEWFKPLAYALILTRE  360
4  SKSGGNYDMRNIFNGTVVQRHPSHAVTFVDNHDSQPEEALESFVEEWFKPLAYALTLTRE  360
```

FIG. 2C

```
       370        380        390        400        410        420
        |          |          |          |          |          |
1  QGYPSVFYGDYYGIPTHGVPAMKSKIDPLLQARQTFAYGTQHDYFDHRDIGWTREGNSS      420
3  EGYPCVFYGDYYGIPTHGVPQYNIPSLKSKIDPLLIARRDYAYGTQHDYLDHSDIGWTREGGTE 418
2  QGYPSVFYGDYYGIPTHSVPAMKAKIDPILEARQNFAYGTQHDYFDHINIGWTREGNTI     420
4  QGYPSVFYGDYYGIPTHGVPAMRSKIDPILEARQKYAYGKQNDYLDHKNIGWTREGNTA     420

430        440        450        460        470        480
        |          |          |          |          |          |
1  HPNSGLATIMSDGPGGNKWMYVGKNKAGQVWRDITGNRTGTVTINADGWGNFSVNGGSVS     480
3  KPGSGLAALITDGPGGSKMMYVGKQHAGKVFYDLIGNRSDTVTINSDGWGEFKVNGGSVS     478
2  HPNSGLATIMSDGPGGEKWMYVGQNKAGQVWHDITGNKPGTVTINADGWANFSVNGGSVS     480
4  HPNSGLATIMSDGAGGSKWMFVGRNKAGQVWSDITGNRTGTVTINADGWGNFSVNGGSVS     480

490        500        510        520        530        540
        |          |          |          |          |          |
1  VWVKQ                                                            485
3  VWVPRKTTVSTIARPITTRPWTGEFVRWTEPRLVAW                             514
2  IWVKR                                                            485
4  IWVNK                                                            485
```

SEQUENCE LISTING

<160> NUMBER OF SEQ ID NOS: 41

<210> SEQ ID NO 1
<211> LENGTH: 1920
<212> TYPE: DNA
<213> ORGANISM: Bacillus licheniformis

<400> SEQUENCE: 1

```
cggaagattg gaagtacaaa aataagcaaa agattgtcaa tcatgtcatg agccatgcgg      60
gagacggaaa aatcgtctta atgcacgata tttatgcaac gttcgcagat gctgctgaag     120
agattattaa aaagctgaaa gcaaaaggct atcaattggt aactgtatct cagcttgaag     180
aagtgaagaa gcagagaggc tattgaataa atgagtagaa gcgccatatc ggcgcttttc     240
ttttggaaga aaatataggg aaaatggtac ttgttaaaaa ttcggaatat ttatacaaca     300
tcatatgttt cacattgaaa ggggaggaga atcatgaaac aacaaaaacg gctttacgcc     360
cgattgctga cgctgttatt tgcgctcatc ttcttgctgc ctcattctgc agcagcggcg     420
gcaaatctta atgggacgct gatgcagtat tttgaatggt acatgcccaa tgacggccaa     480
cattggaggc gtttgcaaaa cgactcggca tatttggctg aacacggtat tactgccgtc     540
tggattcccc cggcatataa gggaacgagc caagcggatg tgggctacgg tgcttacgac     600
ctttatgatt taggggagtt tcatcaaaaa gggacggttc ggacaaagta cggcacaaaa     660
ggagagctgc aatctgcgat caaaagtctt cattcccgcg acattaacgt ttacggggat     720
gtggtcatca accacaaagg cggcgctgat gcgaccgaag atgtaaccgc ggttgaagtc     780
gatcccgctg accgcaaccg cgtaatttca ggagaacacc taattaaagc ctggacacat     840
tttcattttc cggggcgcgg cagcacatac agcgatttta aatggcattg gtaccatttt     900
gacggaaccg attgggacga gtcccgaaag ctgaaccgca tctataagtt tcaaggaaag     960
gcttgggatt gggaagtttc caatgaaaac ggcaactatg attatttgat gtatgccgac    1020
atcgattatg accatcctga tgtcgcagca gaaattaaga gatggggcac ttggtatgcc    1080
aatgaactgc aattggacgg tttccgtctt gatgctgtca aacacattaa attttctttt    1140
ttgcgggatt gggttaatca tgtcagggaa aaaacgggga aggaaatgtt tacggtagct    1200
gaatattggc agaatgactt gggcgcgctg gaaaactatt tgaacaaaac aaattttaat    1260
cattcagtgt ttgacgtgcc gcttcattat cagttccatg ctgcatcgac acagggaggc    1320
ggctatgata tgaggaaatt gctgaacggt acggtcgttt ccaagcatcc gttgaaatcg    1380
gttacatttg tcgataacca tgatacacag ccggggcaat cgcttgagtc gactgtccaa    1440
acatggttta agccgcttgc ttacgctttt attctcacaa gggaatctgg ataccctcag    1500
gttttctacg gggatatgta cgggacgaaa ggagactccc agcgcgaaat tcctgccttg    1560
aaacacaaaa ttgaaccgat cttaaaagcg agaaaacagt atgcgtacgg agcacagcat    1620
gattatttcg accaccatga cattgtcggc tggacaaggg aaggcgacag ctcggttgca    1680
aattcaggtt tggcggcatt aataacagac ggacccggtg gggcaaagcg aatgtatgtc    1740
ggccggcaaa acgccggtga gacatggcat gacattaccg gaaaccgttc ggagccggtt    1800
gtcatcaatt cggaaggctg gggagagttt cacgtaaacg gcgggtcggt ttcaatttat    1860
gttcaaagat agaagagcag agaggacgga tttcctgaag gaaatccgtt tttttatttt    1920
```

<210> SEQ ID NO 2
<211> LENGTH: 483
<212> TYPE: PRT
<213> ORGANISM: Bacillus licheniformis

<400> SEQUENCE: 2

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp

```
                       405                 410                 415
        Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Gly Ser Val Ser Ile Tyr
        465                 470                 475                 480

Val Gln Arg

<210> SEQ ID NO 3
<211> LENGTH: 2084
<212> TYPE: DNA
<213> ORGANISM: Bacillus amyloliquefaciens

<400> SEQUENCE: 3
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg tattttttta tgctgtccag actgtccgct gtgtaaaaat aaggaataaa     180 gggggggttgt tattatttta ctgatatgta aatataatt tgtataagaa atgagaggg     240 agaggaaaca tgattcaaaa acgaaagcgg acagtttcgt tcagacttgt gcttatgtgc     300
acgctgttat ttgtcagttt gccgattaca aaacatcag ccgtaaatgg cacgctgatg     360
cagtattttg aatggtatac gccgaacgac ggccagcatt ggaaacgatt gcagaatgat     420
gcggaacatt tatcggatat cggaatcact gccgtctgga ttcctcccgc atacaaagga     480
ttgagccaat ccgataacgg atacggacct tatgatttgt atgatttagg agaattccag     540
caaaaaggga cggtcagaac gaaatacggc acaaaatcag agcttcaaga tgcgatcggc     600
tcactgcatt cccggaacgt ccaagtatac ggagatgtgg ttttgaatca taaggctggt     660
gctgatgcaa cagaagatgt aactgccgtc gaagtcaatc cggccaatag aaatcaggaa     720
acttcggagg aatatcaaat caaagcgtgg acggattttc gttttccggg ccgtggaaac     780
acgtacagtg attttaaatg gcattggtat catttcgacg agcggactg ggatgaatcc     840 cggaagatca gccgcatctt taagtttcgt ggggaaggaa aagcgtggga ttggaagta     900 tcaagtgaaa acggcaacta tgactattta atgtatgctg atgttgacta cgaccaccct     960
gatgtcgtgg cagagacaaa aaatggggt atctggtatg cgaatgaact gtcattagac    1020
ggcttccgta ttgatgccgc caaacatatt aaatttcat ttctgcgtga ttgggttcag    1080
gcggtcagac aggcgacggg aaaagaaatg tttacggttg cggagtattg gcagaataat    1140
gccgggaaac tcgaaaacta cttgaataaa acaagcttta tcaatccgt gtttgatgtt    1200 ccgcttcatt tcaatttaca ggcggcttcc tcacaaggag gcggatatga tatgaggcgt    1260 tgctggacg gtaccgttgt gtccaggcat ccggaaaagg cggttacatt tgttgaaaat    1320
catgacacac agccgggaca gtcattggaa tcgacagtcc aaacttggtt taaaccgctt    1380
gcatacgcct ttattttgac aagagaatcc ggttatcctc aggtgttcta tgggatatg    1440 tacgggacaa aagggacatc gccaaggaa attccctcac tgaaagataa tatagagccg    1500
attttaaaag cgcgtaagga gtacgcatac gggccccagc acgattatat tgaccacccg    1560
gatgtgatcg gatggacgag ggaaggtgac agctccgccg ccaaatcagg tttggccgct    1620
ttaatcacgg acggacccgg cggatcaaag cggatgtatg ccggcctgaa aaatgccggc    1680
```

```
gagacatggt atgacataac gggcaaccgt tcagatactg taaaaatcgg atctgacggc  1740
tggggagagt tcatgtaaa cgatgggtcc gtctccattt atgttcagaa ataaggtaat   1800
aaaaaaacac ctccaagctg agtgcgggta tcagcttgga ggtgcgttta ttttttcagc  1860
cgtatgacaa ggtcggcatc aggtgtgaca aatacggtat gctggctgtc ataggtgaca  1920
aatccgggtt ttgcgccgtt tggcttttc acatgtctga ttttgtata atcaacaggc    1980 acggagccgg aatctttcgc cttggaaaaa taagcggcga tcgtagctgc ttccaatatg  2040
gattgttcat cgggatcgct gcttttaatc acaacgtggg atcc                  2084
```

<210> SEQ ID NO 4
<211> LENGTH: 480
<212> TYPE: PRT
<213> ORGANISM: Bacillus amyloliquefaciens

<400> SEQUENCE: 4

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
    195                 200                 205

Val Ala Glu Thr Lys Lys Trp Gly Ile Trp Tyr Ala Asn Glu Leu Ser
        210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
    275                 280                 285

His Phe Asn Leu Gln Ala Ala Ser Ser Gln Gly Gly Gly Tyr Asp Met
        290                 295                 300
```

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
    355                 360                 365

Thr Lys Gly Thr Ser Pro Lys Glu Ile Pro Ser Leu Lys Asp Asn Ile
370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
        420                 425                 430

Gly Gly Ser Lys Arg Met Tyr Ala Gly Leu Lys Asn Ala Gly Glu Thr
    435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

<210> SEQ ID NO 5
<211> LENGTH: 1814
<212> TYPE: DNA
<213> ORGANISM: Bacillus stearothermophilus

<400> SEQUENCE: 5
aaattcgata ttgaaaacga ttacaaataa aaattataat agacgtaaac gttcgagggt      60
ttgctccctt tttactcttt ttatgcaatc gtttccctta attttttgga agccaaaccg     120
tcgaatgtaa catttgatta agggggaagg gcattgtgct aacgtttcac cgcatcattc     180
gaaaaggatg gatgttcctg ctcgcgtttt tgctcactgt ctcgctgttc tgcccaacag     240
gacagcccgc caaggctgcc gcaccgttta acggcaccat gatgcagtat tttgaatggt     300
acttgccgga tgatggcacg ttatggacca aagtggccaa tgaagccaac aacttatcca     360
gccttggcat caccgctctt tggctgccgc ccgcttacaa aggaacaagc cgcagcgacg     420
tagggtacgg agtatacgac ttgtatgacc tcggcgaatt caatcaaaaa gggaccgtcc     480
gcacaaaata cggaacaaaa gctcaatatc ttcaagccat tcaagccgcc cacgccgctg     540
gaatgcaagt gtacgccgat gtcgtgttcg accataaagg cggcgctgac ggcacggaat     600
gggtggacgc cgtcgaagtc aatccgtccg accgcaacca gaaatctcg gcacctatc      660 aaatccaagc atggacgaaa tttgattttc ccgggcgggg caacacctac tccagcttta     720
agtggcgctg gtaccatttt gacggcgttg attgggacga agccgaaaa ttgagccgca     780 tttacaaatt ccgcggcatc ggcaaagcgt gggattggga agtagacacg gaaaacggaa     840
actatgacta cttaatgtat gccgaccttg atatggatca tcccgaagtc gtgaccgagc     900
tgaaaaactg ggggaaatgg tatgtcaaca aacgaacat tgatgggttc cggcttgatg     960
ccgtcaagca tattaagttc agtttttttc ctgattggtt gtcgtatgtg cgttctcaga    1020
ctggcaagcc gctatttacc gtcggggaat attggagcta tgacatcaac aagttgcaca    1080
attacattac gaaaacagac ggaacgatgt ctttgtttga tgccccgtta cacaacaaat    1140

```
tttataccgc ttccaaatca gggggcgcat ttgatatgcg cacgttaatg accaatactc    1200
tcatgaaaga tcaaccgaca ttggccgtca ccttcgttga taatcatgac accgaacccg    1260
gccaagcgct gcagtcatgg gtcgacccat ggttcaaacc gttggcttac gcctttattc    1320
taactcggca ggaaggatac ccgtgcgtct tttatggtga ctattatggc attccacaat    1380
ataacattcc ttcgctgaaa agcaaaatcg atccgctcct catcgcgcgc agggattatg    1440
cttacggaac gcaacatgat tatcttgatc actccgacat catcgggtgg acaagggaag    1500
ggggcactga aaaccagga tccggactgg ccgcactgat caccgatggg ccgggaggaa    1560
gcaaatggat gtacgttggc aaacaacacg ctggaaaagt gttctatgac cttaccggca    1620
accggagtga caccgtcacc atcaacagtg atggatgggg ggaattcaaa gtcaatggcg    1680
gttcggtttc ggtttgggtt cctagaaaaa cgaccgtttc taccatcgct cggccgatca    1740
caacccgacc gtggactggt gaattcgtcc gttggaccga accacggttg gtggcatggc    1800
cttgatgcct gcga                                                     1814

<210> SEQ ID NO 6
<211> LENGTH: 514
<212> TYPE: PRT
<213> ORGANISM: Bacillus stearothermophilus

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
```

```
                245                 250                 255
Lys Pro Leu Phe Thr Val Gly Glu Tyr Trp Ser Tyr Asp Ile Asn Lys
            260                 265                 270
Leu His Asn Tyr Ile Thr Lys Thr Asp Gly Thr Met Ser Leu Phe Asp
        275                 280                 285
Ala Pro Leu His Asn Lys Phe Tyr Thr Ala Ser Lys Ser Gly Gly Ala
    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Gly
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
        435                 440                 445
Phe Tyr Asp Leu Thr Gly Asn Arg Ser Asp Thr Val Thr Ile Asn Ser
    450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
                485                 490                 495
Arg Pro Trp Thr Gly Glu Phe Val Arg Trp Thr Glu Pro Arg Leu Val
            500                 505                 510
Ala Trp

<210> SEQ ID NO 7
<211> LENGTH: 478
<212> TYPE: PRT
<213> ORGANISM: Bacillus licheniformis

<400> SEQUENCE: 7

Ala Thr Pro Ala Asp Trp Arg Ser Gln Ser Ile Tyr Phe Leu Leu Thr
1               5                   10                  15
Asp Arg Phe Ala Arg Thr Asp Gly Ser Thr Thr Ala Thr Cys Asn Thr
            20                  25                  30
Ala Asp Gln Lys Tyr Cys Gly Gly Thr Trp Gln Gly Ile Ile Asp Lys
        35                  40                  45
Leu Asp Tyr Ile Gln Gly Met Gly Phe Thr Ala Ile Trp Ile Thr Pro
    50                  55                  60
Val Thr Ala Gln Leu Pro Gln Thr Thr Ala Tyr Gly Asp Ala Tyr His
65                  70                  75                  80
Gly Tyr Trp Gln Gln Asp Ile Tyr Ser Leu Asn Glu Asn Tyr Gly Thr
                85                  90                  95
Ala Asp Asp Leu Lys Ala Leu Ser Ser Ala Leu His Glu Arg Gly Met
```

100             105             110
Tyr Leu Met Val Asp Val Ala Asn His Met Gly Tyr Asp Gly Ala
        115             120             125

Gly Ser Ser Val Asp Tyr Ser Val Phe Lys Pro Phe Ser Ser Gln Asp
    130             135             140

Tyr Phe His Pro Phe Cys Phe Ile Gln Asn Tyr Glu Asp Gln Thr Gln
145             150             155             160

Val Glu Asp Cys Trp Leu Gly Asp Asn Thr Val Ser Leu Pro Asp Leu
                165             170             175

Asp Thr Thr Lys Asp Val Val Lys Asn Glu Trp Tyr Asp Trp Val Gly
            180             185             190

Ser Leu Val Ser Asn Tyr Ser Ile Asp Gly Leu Arg Ile Asp Thr Val
        195             200             205

Lys His Val Gln Lys Asp Phe Trp Pro Gly Tyr Asn Lys Ala Ala Gly
    210             215             220

Val Tyr Cys Ile Gly Glu Val Leu Asp Gly Asp Pro Ala Tyr Thr Cys
225             230             235             240

Pro Tyr Gln Asn Val Met Asp Gly Val Leu Asn Tyr Pro Ile Tyr Tyr
                245             250             255

Pro Leu Leu Asn Ala Phe Lys Ser Thr Ser Gly Ser Met Asp Asp Leu
            260             265             270

Tyr Asn Met Ile Asn Thr Val Lys Ser Asp Cys Pro Asp Ser Thr Leu
        275             280             285

Leu Gly Thr Phe Val Glu Asn His Asp Asn Pro Arg Phe Ala Ser Tyr
    290             295             300

Thr Asn Asp Ile Ala Leu Ala Lys Asn Val Ala Ala Phe Ile Ile Leu
305             310             315             320

Asn Asp Gly Ile Pro Ile Ile Tyr Ala Gly Gln Glu Gln His Tyr Ala
                325             330             335

Gly Gly Asn Asp Pro Ala Asn Arg Glu Ala Thr Trp Leu Ser Gly Tyr
            340             345             350

Pro Thr Asp Ser Glu Leu Tyr Lys Leu Ile Ala Ser Ala Asn Ala Ile
        355             360             365

Arg Asn Tyr Ala Ile Ser Lys Asp Thr Gly Phe Val Thr Tyr Lys Asn
    370             375             380

Trp Pro Ile Tyr Lys Asp Asp Ile Thr Ile Ala Met Arg Lys Gly Thr
385             390             395             400

Asp Gly Ser Gln Ile Val Thr Ile Leu Ser Asn Lys Gly Ala Ser Gly
                405             410             415

Asp Ser Tyr Thr Leu Ser Leu Ser Gly Ala Gly Tyr Thr Ala Gly Gln
            420             425             430

Gln Leu Thr Glu Val Ile Gly Cys Thr Thr Val Thr Val Gly Ser Asp
        435             440             445

Gly Asn Val Pro Val Pro Met Ala Gly Gly Leu Pro Arg Val Leu Tyr
    450             455             460

Pro Thr Glu Lys Leu Ala Gly Ser Lys Ile Cys Ser Ser Ser
465             470             475

<210> SEQ ID NO 8
<211> LENGTH: 20
<212> TYPE: DNA
<213> ORGANISM: Bacillus amyloliquefaciens

<400> SEQUENCE: 8
gacctgcagt caggcaacta                                                    20

<210> SEQ ID NO 9
<211> LENGTH: 20
<212> TYPE: DNA
<213> ORGANISM: Bacillus amyloliquefaciens

<400> SEQUENCE: 9
tagagtcgac ctgcaggcat                                                    20

<210> SEQ ID NO 10
<211> LENGTH: 31
<212> TYPE: DNA
<213> ORGANISM: Bacillus licheniformis

<400> SEQUENCE: 10
ggtcgtaggc accgtagccc caatccgctt g                                       31

<210> SEQ ID NO 11
<211> LENGTH: 36
<212> TYPE: DNA
<213> ORGANISM: Bacillus licheniformis

<400> SEQUENCE: 11
ggtcgtaggc accgtagccc caatcccatt ggctcg                                  36

<210> SEQ ID NO 12
<211> LENGTH: 28
<212> TYPE: DNA
<213> ORGANISM: Bacillus licheniformis

<400> SEQUENCE: 12
ctgtgactgg tgagtactca accaagtc                                           28

<210> SEQ ID NO 13
<211> LENGTH: 31
<212> TYPE: DNA
<213> ORGANISM: Bacillus licheniformis

<400> SEQUENCE: 13
ggtcgtaggc accgtagccc tcatccgctt g                                       31

<210> SEQ ID NO 14
<211> LENGTH: 31
<212> TYPE: DNA
<213> ORGANISM: Bacillus licheniformis

<400> SEQUENCE: 14
ggtcgtaggc accgtagccc atatccgctt g                                       31

<210> SEQ ID NO 15
<211> LENGTH: 31
<212> TYPE: DNA
<213> ORGANISM: Bacillus licheniformis

<400> SEQUENCE: 15
ggtcgtaggc accgtagcca atatccgctt g                                       31

<210> SEQ ID NO 16
<211> LENGTH: 36
<212> TYPE: DNA
<213> ORGANISM: Bacillus licheniformis

<400> SEQUENCE: 16

```
gcagcatgga actgctyatg aagaggcacg tcaaac                           36

<210> SEQ ID NO 17
<211> LENGTH: 30
<212> TYPE: DNA
<213> ORGANISM: Bacillus licheniformis

<400> SEQUENCE: 17
catagttgcc gaattcattg gaaacttccc                                  30

<210> SEQ ID NO 18
<211> LENGTH: 34
<212> TYPE: DNA
<213> ORGANISM: Bacillus licheniformis

<400> SEQUENCE: 18
catagttgcc gaattcaggg gaaacttccc aatc                             34

<210> SEQ ID NO 19
<211> LENGTH: 41
<212> TYPE: DNA
<213> ORGANISM: Bacillus licheniformis

<400> SEQUENCE: 19
ccgcgccccg ggaaatcaaa ttttgtccag gctttaatta g                     41

<210> SEQ ID NO 20
<211> LENGTH: 32
<212> TYPE: DNA
<213> ORGANISM: Bacillus licheniformis

<400> SEQUENCE: 20
caaaatggta ccaataccac ttaaaatcgc tg                               32

<210> SEQ ID NO 21
<211> LENGTH: 29
<212> TYPE: DNA
<213> ORGANISM: Bacillus licheniformis

<400> SEQUENCE: 21
cttcccaatc ccaagtcttc ccttgaaac                                   29

<210> SEQ ID NO 22
<211> LENGTH: 36
<212> TYPE: DNA
<213> ORGANISM: Bacillus licheniformis

<400> SEQUENCE: 22
cttaatttct gctacgacgt caggatggtc ataatc                           36

<210> SEQ ID NO 23
<211> LENGTH: 38
<212> TYPE: DNA
<213> ORGANISM: Bacillus licheniformis

<400> SEQUENCE: 23
cgcccaagtc attcgaccag tactcagcta ccgtaaac                         38

<210> SEQ ID NO 24
<211> LENGTH: 29
<212> TYPE: DNA
<213> ORGANISM: Bacillus licheniformis
```

```
<400> SEQUENCE: 24
gccgttttca ttgtcgactt cccaatccc                                    29

<210> SEQ ID NO 25
<211> LENGTH: 35
<212> TYPE: DNA
<213> ORGANISM: Bacillus licheniformis

<400> SEQUENCE: 25
ggaatttcgc gctgactagt cccgtacata tcccc                             35

<210> SEQ ID NO 26
<211> LENGTH: 36
<212> TYPE: DNA
<213> ORGANISM: Bacillus licheniformis

<400> SEQUENCE: 26
ggcaggaatt tcgcgacctt tcgtcccgta catatc                            36

<210> SEQ ID NO 27
<211> LENGTH: 36
<212> TYPE: DNA
<213> ORGANISM: Bacillus amyloliquefaciens

<400> SEQUENCE: 27
cctcattctg cagcagcagc cgtaaatggc acgctg                            36

<210> SEQ ID NO 28
<211> LENGTH: 38
<212> TYPE: DNA
<213> ORGANISM: Bacillus amyloliquefaciens

<400> SEQUENCE: 28
ccagacggca gtaataccga tatccgataa atgttccg                          38

<210> SEQ ID NO 29
<211> LENGTH: 30
<212> TYPE: DNA
<213> ORGANISM: Bacillus amyloliquefaciens

<400> SEQUENCE: 29
cggatatcgg tattactgcc gtctggattc                                   30

<210> SEQ ID NO 30
<211> LENGTH: 21
<212> TYPE: DNA
<213> ORGANISM: Bacillus amyloliquefaciens

<400> SEQUENCE: 30
ctcgtcccaa tcggttccgt c                                            21

<210> SEQ ID NO 31
<211> LENGTH: 75
<212> TYPE: DNA
<213> ORGANISM: Bacillus licheniformis

<400> SEQUENCE: 31
cgcggcagca catacagcga ttwtvawtgg drttggwmty attttgacgg aamcgattgg  60
gacgagtccc gaaag                                                   75

<210> SEQ ID NO 32
<211> LENGTH: 84
```

<212> TYPE: DNA
<213> ORGANISM: Bacillus licheniformis

<400> SEQUENCE: 32
ctgaaccgca tctataagtt tmakrstaag rmktgggatw sggakgttav tmmtgaathk    60
rskaactatg attatttgat gtat                                          84

<210> SEQ ID NO 33
<211> LENGTH: 72
<212> TYPE: DNA
<213> ORGANISM: Bacillus licheniformis
<220> FEATURE:
<221> NAME/KEY: misc_feature
<222> LOCATION: (37)..(37)
<223> OTHER INFORMATION: N at position 37 is G, A, T, or C

<400> SEQUENCE: 33
tatgccgaca tcgattatga cyrthctdmw vttrwrnmts akwtwaramr atggggcact    60
tggtatgcca at                                                       72

<210> SEQ ID NO 34
<211> LENGTH: 78
<212> TYPE: DNA
<213> ORGANISM: Bacillus licheniformis
<220> FEATURE:
<221> NAME/KEY: misc_feature
<222> LOCATION: (31)..(31)
<223> OTHER INFORMATION: N at position 31 is C, T, A, or G

<400> SEQUENCE: 34
ttggacggtt tccgtcttga tdytgytaaa nwwmttargt wtwmttwtht wmvggawtgg    60
gttaatcatg tcagggaa                                                 78

<210> SEQ ID NO 35
<211> LENGTH: 63
<212> TYPE: DNA
<213> ORGANISM: Bacillus licheniformis

<400> SEQUENCE: 35
gctgaccgca accgcgtaat ttcarskgak hhtwbawtaa rggcctggac acattttcat    60
ttt                                                                 63

<210> SEQ ID NO 36
<211> LENGTH: 78
<212> TYPE: DNA
<213> ORGANISM: Bacillus licheniformis

<400> SEQUENCE: 36
tggtaccatt ttgacggaac cgattggrak gagdcgcgaa rgmwaavtar gdwytwtaag    60
tttcaaggaa aggcttgg                                                 78

<210> SEQ ID NO 37
<211> LENGTH: 93
<212> TYPE: DNA
<213> ORGANISM: Bacillus licheniformis
<220> FEATURE:
<221> NAME/KEY: Misc_feature
<222> LOCATION: (43)..(43)
<223> OTHER INFORMATION: N at position 43 is G, T, or C

<400> SEQUENCE: 37
gaaatgttta cggtagctga atwttggrvk wvtrawhyrr stnytmtkga wavttwtwtr    60
avcargacar attttaatca ttcagtgttt gac					93

<210> SEQ ID NO 38
<211> LENGTH: 485
<212> TYPE: PRT
<213> ORGANISM: Unknown
<220> FEATURE:
<223> OTHER INFORMATION: Bacillus species

<400> SEQUENCE: 38

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
```

```
                355                 360                 365
Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
            450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 39
<211> LENGTH: 485
<212> TYPE: PRT
<213> ORGANISM: Unknown
<220> FEATURE:
<223> OTHER INFORMATION: Bacillus species

<400> SEQUENCE: 39

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
```

```
                225                 230                 235                 240
Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
                260                 265                 270

Gly Ala Leu Glu Asn Tyr Leu Asn Lys Thr Asn Trp Asn His Ser Val
                275                 280                 285

Phe Asp Val Pro Leu His Tyr Asn Leu Tyr Asn Ala Ser Asn Ser Gly
                290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
                340                 345                 350

Tyr Ala Leu Ile Leu Thr Arg Glu Gln Gly Tyr Pro Ser Val Phe Tyr
                355                 360                 365

Gly Asp Tyr Tyr Gly Ile Pro Thr His Ser Val Pro Ala Met Lys Ala
                370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
                435                 440                 445

Gln Val Trp His Asp Ile Thr Gly Asn Lys Pro Gly Thr Val Thr Ile
                450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 40
<211> LENGTH: 485
<212> TYPE: PRT
<213> ORGANISM: Unknown
<220> FEATURE:
<223> OTHER INFORMATION: Bacillus species

<400> SEQUENCE: 40

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
                35                  40                  45

Lys Gly Ala Ser Gln Asn Asp Val Gly Tyr Gly Ala Tyr Asp Leu Tyr
                50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
```

```
            100                 105                 110
Ala Thr Glu Met Val Arg Ala Glu Val Asn Pro Asn Arg Asn
        115                 120                 125

Gln Glu Val Thr Gly Glu Tyr Thr Ile Glu Ala Trp Thr Arg Phe Asp
            130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
            210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Gln Lys Thr Asn Trp Asn His Ser Val
                275                 280                 285

Phe Asp Val Pro Leu His Tyr Asn Leu Tyr Asn Ala Ser Lys Ser Gly
            290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Arg Ser
            370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 41
<211> LENGTH: 1458
<212> TYPE: DNA
<213> ORGANISM: Unknown
```

<220> FEATURE:
<223> OTHER INFORMATION: Bacillus species

<400> SEQUENCE: 41

```
catcataatg gaacaaatgg tactatgatg caatatttcg aatggtattt gccaaatgac      60
gggaatcatt ggaacaggtt gagggatgac gcagctaact taaagagtaa agggataaca     120
gctgtatgga tcccacctgc atggaagggg acttcccaga atgatgtagg ttatggagcc     180
tatgatttat atgatcttgg agagtttaac cagaagggga cggttcgtac aaaatatgga     240
acacgcaacc agctacaggc tgcggtgacc tctttaaaaa ataacggcat tcaggtatat     300
ggtgatgtcg tcatgaatca taaaggtgga gcagatggta cggaaattgt aaatgcggta     360
gaagtgaatc ggagcaaccg aaaccaggaa acctcaggag agtatgcaat agaagcgtgg     420
acaaagtttg attttcctgg aagaggaaat aaccattcca gctttaagtg gcgctggtat     480
cattttgatg ggacagattg ggatcagtca cgccagcttc aaaacaaaat atataaattc     540
aggggaacag gcaaggcctg ggactgggaa gtcgatacag agaatggcaa ctatgactat     600
cttatgtatg cagacgtgga tatggatcac ccagaagtaa tacatgaact tagaaactgg     660
ggagtgtggt atacgaatac actgaacctt gatggattta gaatagatgc agtgaaacat     720
ataaaatata gctttacgag agattggctt acacatgtgc gtaacaccac aggtaaacca     780
atgtttgcag tggctgagtt ttggaaaaat gaccttggtg caattgaaaa ctatttgaat     840
aaaacaagtt ggaatcactc ggtgtttgat gttcctctcc actataattt gtacaatgca     900
tctaatagcg gtggttatta tgatatgaga aatatttaa atggttctgt ggtgcaaaaa     960
catccaacac atgccgttac ttttgttgat aaccatgatt ctcagcccgg ggaagcattg    1020
gaatcctttg ttcaacaatg gtttaaacca cttgcatatg cattggttct gacaagggaa    1080
caaggttatc cttccgtatt ttatgggga tactacggta tcccaaccca tggtgttccg    1140
gctatgaaat ctaaataga ccctcttctg caggcacgtc aaacttttgc ctatggtacg    1200
cagcatgatt actttgatca tcatgatatt atcggttgga caagagaggg aaatagctcc    1260
catccaaatt caggccttgc caccattatg tcagatggtc caggtggtaa caaatggatg    1320
tatgtgggga aaaataaagc gggacaagtt tggagagata ttaccggaaa taggacaggc    1380
accgtcacaa ttaatgcaga cggatggggt aatttctctg ttaatggagg gtccgtttcg    1440
gtttgggtga agcaataa                                                 1458
```

US 9,487,769 B2

ALPHA-AMYLASE MUTANTS

CROSS-REFERENCE TO RELATED APPLICATIONS

This application is a division of U.S. application Ser. No. 13/953,409 filed Jul. 29, 2013 (now U.S. Pat. No. 8,999,908), which is a division of U.S. application Ser. No. 13/557,313 filed Jul. 25, 2012 (now U.S. Pat. No. 8,513,175), which is a division of U.S. application Ser. No. 13/100,407 filed May 4, 2011, now U.S. Pat. No. 8,263,382, which is a continuation of U.S. application Ser. No. 11/862,580 filed Sep. 27, 2007, now U.S. Pat. No. 7,960,161, which is a division of U.S. application Ser. No. 10/980,759 filed Nov. 3, 2004, now U.S. Pat. No. 7,625,737, which is a continuation of U.S. application Ser. No. 10/644,187 filed Aug. 20, 2003, now abandoned, which is a division of U.S. application Ser. No. 10/186,042 filed Jun. 28, 2002, now U.S. Pat. No. 6,642,044, which is a division of U.S. application Ser. No. 09/672,459 filed Sep. 28, 2000, now U.S. Pat. No. 6,436,888, which is a continuation of U.S. application Ser. No. 09/182,859 filed Oct. 29, 1998, now U.S. Pat. No. 6,143,708, which is a continuation of international application no. PCT/DK97/00197 filed Apr. 30, 1997, which claims priority under 35 U.S.C. 119 of Danish application nos. 0515/96, 0712/96, 0775/96, and 1263/96 filed Apr. 30, 1996, Jun. 28, 1996, Jul. 11, 1996, and Nov. 8, 1996, respectively, the contents of which are fully incorporated herein by reference.

FIELD OF THE INVENTION

The present invention relates, inter alia, to novel variants (mutants) of parent Termamyl-like alpha-amylases, notably variants exhibiting alterations in one or more properties (relative to the parent) which are advantageous with respect to applications of the variants in, in particular, industrial starch processing (e.g., starch liquefaction or saccharification).

BACKGROUND OF THE INVENTION

Alpha-amylases (alpha-1,4-glucan-4-glucanohydrolases, EC 3.2.1.1) constitute a group of enzymes which catalyze hydrolysis of starch and other linear and branched 1,4-glucosidic oligo- and polysaccharides, and there is a very extensive body of patent and scientific literature relating to this industrially very important class of enzymes.

Among more recent disclosures relating to alpha-amylases, WO 96/23874 provides three-dimensional, X-ray crystal structural data for a Termamyl-like alpha-amylase which consists of the 300 N-terminal amino acid residues of the *B. amyloliquefaciens* alpha-amylase comprising the amino acid sequence shown in SEQ ID NO: 4 and amino acids 301-483 of the C-terminal end of the *B. licheniformis* alpha-amylase comprising the amino acid sequence shown in SEQ ID NO: 2 (the latter being available commercially under the tradename Termamyl™), and which is thus closely related to the industrially important *Bacillus* alpha-amylases (which in the present context are embraced within the meaning of the term "Termamyl-like alpha-amylases", and which include, inter alia, the *B. licheniformis*, *B. amyloliquefaciens* and *B. stearothermophilus* alpha-amylases). WO 96/23874 further describes methodology for designing, on the basis of an analysis of the structure of a parent Termamyl-like alpha-amylase, variants of the parent Termamyl-like alpha-amylase which exhibit altered properties relative to the parent.

SUMMARY OF THE INVENTION

As indicated above, the present invention relates, inter alia, to novel alpha-amylolytic variants (mutants) of a Termamyl-like alpha-amylase, in particular variants exhibiting altered properties which are advantageous in connection with the industrial processing of starch (starch liquefaction, saccharification and the like).

Alterations in properties which may be achieved in mutants of the invention are alterations in, e.g., substrate specificity, substrate binding, substrate cleavage pattern, thermal stability, pH/activity profile, pH/stability profile [such as increased stability at low (e.g., pH<6, in particular pH<5) or high (e.g., pH>9) pH values], stability towards oxidation, $Ca^{2+}$ dependency, specific activity, and other properties of interest. For instance, the alteration may result in a variant which, as compared to the parent Termamyl-like alpha-amylase, has a reduced $Ca^{2+}$ dependency and/or an altered pH/activity profile.

The invention further relates, inter alia, to DNA constructs encoding variants of the invention, to methods for preparing variants of the invention, and to the use of variants of the invention, alone or in combination with other alpha-amylolytic enzymes, in various industrial processes, e.g., starch liquefaction.

BRIEF DESCRIPTION OF THE DRAWINGS

FIGS. 1(*a*), 1(*b*), 1(*c*), 1(*d*) and 1(*e*) show the DNA sequence, together with the stop codon TAA, encoding the *Bacillus* strain NCIB 12512 alpha-amylase described in WO 95/26397, together with the amino acid sequence of the encoded alpha-amylase (SEQ ID NOS: 38 and 41).

FIGS. 2(*a*), 2(*b*) and 2(*c*) show an alignment of the amino acid sequences of four parent Termamyl-like alpha-amylases in the context of the invention:

Figure 3:
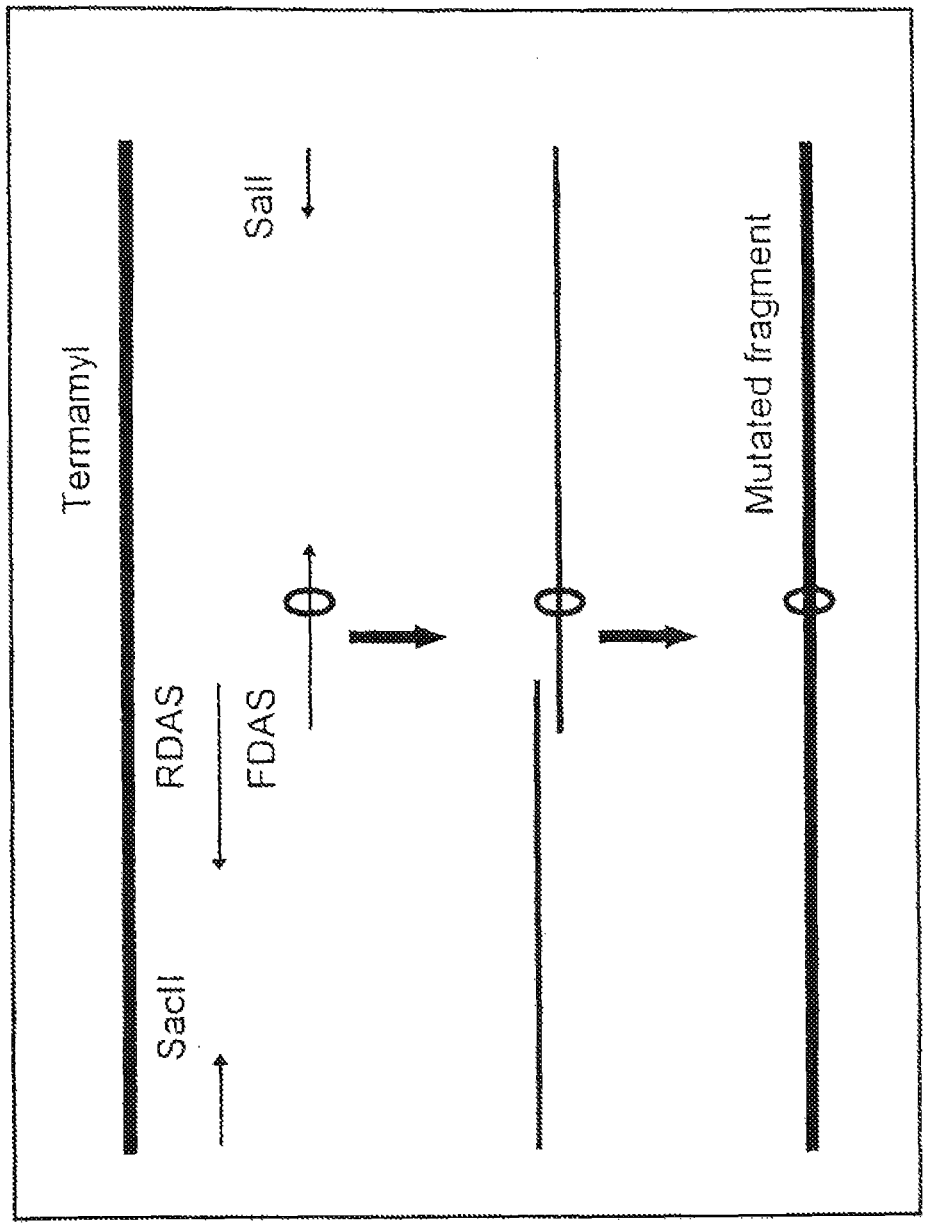

1: the amino acid sequence of the *Bacillus* strain NCIB 12512 alpha-amylase described in WO 95/26397 (SEQ ID NO: 38);

2: the amino acid sequence of the *Bacillus* strain NCIB 12513 alpha-amylase described in WO 95/26397 (SEQ ID NO: 39);

3: the amino acid sequence of the *B. stearothermophilus* alpha-amylase as shown in SEQ ID NO: 6;

4: the amino acid sequence of the *Bacillus* sp. #707 alpha-amylase described by Tsukamoto et al., 1988, *Biochem. Biophys. Res. Commun.* 151: 25-31 (SEQ ID NO: 40).

The numbers on the extreme right of the figure give the running total number of amino acids for each of the sequences in question. Note that for the sequence numbered 3 (corresponding to the sequence in SEQ ID NO: 6), the alignment results in "gaps" at the positions corresponding to amino acid nos. 1 and 175 in the sequences numbered 1, 2 and 4.

FIG. 3 illustrates a PCR strategy employed in Example 2.

DETAILED DISCLOSURE OF THE INVENTION

The Termamyl-Like Alpha-Amylase

It is well known that a number of alpha-amylases produced by *Bacillus* spp. are highly homologous on the amino acid level. For instance, the *B. licheniformis* alpha-amylase comprising the amino acid sequence shown in SEQ ID NO:

2 (commercially available as Termamyl™) has been found to be about 89% homologous with the *B. amyloliquefaciens* alpha-amylase comprising the amino acid sequence shown in SEQ ID NO: 4 and about 79% homologous with the *B. stearothermophilus* alpha-amylase comprising the amino acid sequence shown in SEQ ID NO: 6. Further homologous alpha-amylases include an alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., 1988, *Biochemical and Biophysical Research Communications* 151: 25-31. Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like *B. licheniformis* alpha-amylases are Optitherm™ and Takatherm™ (available from Solvay), Maxamyl™ (available from Gist-brocades/Genencor), Spezym AA™ (available from Genencor), and Keistase™ (available from Daiwa).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase which, at the amino acid level, exhibits a substantial homology to Termamyl™, i.e., the *B. licheniformis* alpha-amylase having the amino acid sequence shown in SEQ ID NO: 2. In other words, a Termamyl-like alpha-amylase is an alpha-amylase which has the amino acid sequence shown in SEQ ID NO: 2, 4 or 6, or the amino acid sequence shown in SEQ ID NO: 1 of WO 95/26397 (which amino acid sequence is shown in FIG. 1 and FIG. 2) or in SEQ ID NO: 2 of WO 95/26397 (which amino acid sequence is shown in FIG. 2) or in Tsukamoto et al. (1988) (which amino acid sequence is shown in FIG. 2) or i) which displays at least 60%, such as at least 70%, e.g., at least 75%, or at least 80%, e.g., at least 85%, at least 90% or at least 95% homology with at least one of said amino acid sequences and/or ii) displays immunological cross-reactivity with an antibody raised against at least one of said alpha-amylases, and/or iii) is encoded by a DNA sequence which hybridizes to the DNA sequences encoding the above-specified alpha-amylases which are apparent from SEQ ID NOs: 1, 3 and 5 of the present application (which encoding sequences encode the amino acid sequences shown in SEQ ID NOs: 2, 4 and 6, respectively), from SEQ ID NO: 4 of WO 95/26397 (which DNA sequence, together with the stop codon TAA, is shown in FIG. 1 and encodes the amino acid sequence shown in FIG. 1) and from SEQ ID NO: 5 of WO 95/26397, respectively.

In connection with property i), the "homology" may be determined by use of any conventional algorithm, preferably by use of the GAP program from the GCG package version 7.3 (June 1993) using default values for GAP penalties [Genetic Computer Group (1991) Programme Manual for the GCG Package, version 7, 575 Science Drive, Madison, Wis., USA 53711].

Property ii) of the alpha-amylase, i.e., the immunological cross reactivity, may be assayed using an antibody raised against, or reactive with, at least one epitope of the relevant Termamyl-like alpha-amylase. The antibody, which may either be monoclonal or polyclonal, may be produced by methods known in the art, e.g., as described by Hudson et al., 1989. The immunological cross-reactivity may be determined using assays known in the art, examples of which are Western Blotting or radial immunodiffusion assay, e.g., as described by Hudson et al., 1989. In this respect, immunological cross-reactivity between the alpha-amylases having the amino acid sequences SEQ ID NOs: 2, 4 and 6, respectively, has been found.

The oligonucleotide probe used in the characterization of the Termamyl-like alpha-amylase in accordance with property iii) above may suitably be prepared on the basis of the full or partial nucleotide or amino acid sequence of the alpha-amylase in question. Suitable conditions for testing hybridization involve presoaking in 5×SSC and prehybridizing for 1 hour at ~40° C. in a solution of 20% formamide, 5×Denhardt's solution, 50 mM sodium phosphate, pH 6.8, and 50 micrograms of denatured sonicated calf thymus DNA, followed by hybridization in the same solution supplemented with 100 micro-M ATP for 18 hours at ~40° C., or other methods described by, e.g., Sambrook et al., 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant which is the result of a modification (insertion, substitution, deletion) of one or more amino acid residues of the naturally occurring alpha-amylase.

Parent Hybrid Alpha-Amylases

The parent alpha-amylase may be a hybrid alpha-amylase, i.e., an alpha-amylase which comprises a combination of partial amino acid sequences derived from at least two alpha-amylases.

The parent hybrid alpha-amylase may be one which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives may, e.g., be any of those specific Termamyl-like alpha-amylase referred to herein.

For instance, the parent alpha-amylase may comprise a C-terminal part of an alpha-amylase derived from a strain of *B. licheniformis*, and an N-terminal part of an alpha-amylase derived from a strain of *B. amyloliquefaciens* or from a strain of *B. stearothermophilus*. For instance, the parent alpha-amylase may comprise at least 430 amino acid residues of the C-terminal part of the *B. licheniformis* alpha-amylase, and may, e.g., comprise a) an amino acid segment corresponding to the 37 N-terminal amino acid residues of the *B. amyloliquefaciens* alpha-amylase having the amino acid sequence shown in SEQ ID NO: 4 and an amino acid segment corresponding to the 445 C-terminal amino acid residues of the *B. licheniformis* alpha-amylase having the amino acid sequence shown in SEQ ID NO: 2, or b) an amino acid segment corresponding to the 68 N-terminal amino acid residues of the *B. stearothermophilus* alpha-amylase having the amino acid sequence shown in SEQ ID NO: 6 and an amino acid segment corresponding to the 415 C-terminal amino acid residues of the *B. licheniformis* alpha-amylase having the amino acid sequence shown in SEQ ID NO: 2.

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures which are markedly different from the structure of a typical Termamyl-like alpha-amylase as referred to herein.

The fungal alpha-amylases mentioned above, i.e., derived from *A. niger* and *A. oryzae*, are highly homologous on the amino acid level and generally considered to belong to the same family of alpha-amylases. The fungal alpha-amylase derived from *Aspergillus oryzae* is commercially available under the tradename Fungamyl™.

Furthermore, when a particular variant of a Termamyl-like alpha-amylase (variant of the invention) is referred to—in a conventional manner—by reference to modification (e.g., deletion or substitution) of specific amino acid residues in the amino acid sequence of a specific Termamyl-like alpha-amylase, it is to be understood that variants of another Termamyl-like alpha-amylase modified in the equivalent position(s) (as determined from the best possible amino acid sequence alignment between the respective amino acid sequences) are encompassed thereby.

A preferred embodiment of a variant of the invention is one derived from a *B. licheniformis* alpha-amylase (as the parent Termamyl-like alpha-amylase), e.g., one of those referred to above, such as the *B. licheniformis* alpha-amylase having the amino acid sequence shown in SEQ ID NO: 2.

Construction of Variants of the Invention

The construction of the variant of interest may be accomplished by cultivating a microorganism comprising a DNA sequence encoding the variant under conditions which are conducive for producing the variant. The variant may then subsequently be recovered from the resulting culture broth. This is described in detail further below.

Altered Properties of Variants of the Invention

The following discusses the relationship between mutations which may be present in variants of the invention, and desirable alterations in properties (relative to those a parent, Termamyl-like alpha-amylase) which may result therefrom.

Decreased $Ca^{2+}$ Dependency

It is highly desirable to be able to decrease the $Ca^{2+}$ dependency of a Termamyl-like alpha-amylase. Accordingly, one aspect of the invention relates to a variant of a parent Termamyl-like alpha-amylase, which variant exhibits alpha-amylase activity and has a decreased $Ca^{2+}$ dependency as compared to the parent alpha-amylase. Decreased $Ca^{2+}$ dependency will in general have the functional consequence that the variant exhibits a satisfactory amylolytic activity in the presence of a lower concentration of calcium ion in the extraneous medium than is necessary for the parent enzyme. It will further often have the consequence that the variant is less sensitive than the parent to calcium ion-depleting conditions such as those obtained in media containing calcium-complexing agents (such as certain detergent builders).

Decreased $Ca^{2+}$ dependency of a variant of the invention may advantageously be achieved, for example, by increasing the $Ca^{2+}$ binding affinity relative to that of the parent Termamyl-like alpha-amylase; in other words the stronger the binding of $Ca^{2+}$ in the enzyme, the lower the $Ca^{2+}$ dependency.

It may be mentioned here that WO 96/23874 states that amino acid residues located within 10 Å from a sodium or calcium ion are believed to be involved in, or of importance for, the $Ca^{2+}$ binding capability of the enzyme, and that in this connection the mutation N104D [of the *B. licheniformis* alpha-amylase having the amino acid sequence shown in SEQ ID NO: 2, or an equivalent (N to D) mutation of an equivalent position in another Termamyl-like alpha-amylase] is contemplated to be of particular interest with respect to decreasing the $Ca^{2+}$ dependency of a Termamyl-like alpha-amylase.

Other mutations mentioned in WO 96/23874 as being of possible importance in connection with $Ca^{2+}$ dependency include mutations which are contemplated therein to achieve increased calcium binding (and/or thermostability of the enzyme) via stabilization of the C-domain (as defined in WO 96/23874) of the three-dimensional structure of a Termamyl-like alpha-amylase via formation, for example, of cysteine bridges or salt bridges. Thus, WO 96/23874 discloses that the C-domain of the *B. licheniformis* alpha-amylase having the amino acid sequence shown in SEQ ID NO: 2 may be stabilized by introduction of a cysteine bridge between domain A and domain C (as defined in WO 96/23874) by introduction of the following mutations: A349C+I479C and/or L346C+I430C.

WO 96/23874 likewise discloses that a salt bridge may be obtained by introduction of one or more of the following mutations in the *B. licheniformis* alpha-amylase having the amino acid sequence shown in SEQ ID NO: 2:
N457D,E
N457D,E+K385R
F350D,E+I430R,K
F350D,E+I411R,K and that the calcium site of Domain C may be stabilized by replacing the amino acid residues H408 and/or G303 with any other amino acid residue, in particular by introducing one of the substitutions:
H408Q,E,N,D and/or G303N,D,Q,E
which are contemplated to provide better calcium binding or protection from calcium depletion (similar mutations in equivalent positions of other Termamyl-like alpha-amylases are encompassed hereby).

Other substitution mutations (relative to *B. licheniformis* alpha-amylase, SEQ ID NO: 2) which are disclosed in WO 96/23874 as being of apparent importance, inter alia, in the context of reducing calcium dependency include the following: R23K, H156Y, A181T, A209V, R214, G310D and P345 (or equivalent mutations in equivalent positions in another Termamyl-like alpha-amylase).

In the context of the present invention, further substitution mutations which appear to be of importance, inter alia, in relation to reduction of calcium dependency include the following mutations in Domain B (as defined in WO 96/23874):

A181E,D,Q,N,V (which appear to result in shielding of the outermost $Ca^{2+}$ binding site in the junction region between Domain A and Domain B to some extent);

I201 (bulkier amino acid), e.g., I201 W,F,L (which appear to result in slight alterations in the geometry of the region in the immediate vicinity of the $Ca^{2+}$—$Na^+$—$Ca^{2+}$ binding site(s) in the junction region between Domain A and Domain B, and in the geometry and/or size of a nearby hole/cavity); and Y203E,Q (which are believed to result in stronger binding of the outermost $Ca^{2+}$ ion in its binding site in the junction region between Domain A and Domain B);
(or equivalent mutations in equivalent positions in another Termamyl-like alpha-amylase).

Altered pH Optimum (Altered pH/Activity Profile)

WO 96/23874 discloses that it is contemplated to be possible to change the pH optimum of a Termamyl-like alpha-amylase, or the enzymatic activity thereof at a given pH, by changing the pKa of the active site residues, and that this may be achieved, e.g., by changing the electrostatic interaction or hydrophobic interaction between functional groups of amino acid side chains of the amino acid residue to be modified and of its close surroundings.

In the context of the present invention, it is believed on the basis of electrostatic considerations [see, e.g., Gilson, 1995, Current Opinion in Structural Biology 5: 216-223; and Honig and Nicholls, 1995, Science 268: 1144-1149; and references given therein] and hygroscopicity considerations in relation to the three-dimensional structure of the Termamyl-like alpha-amylase disclosed in WO 96/23874 that mutations of relevance, inter alia, for altering (increasing or decreasing) the pH optimum of a Termamyl-like alpha-amylase include the following mutations or equivalents thereof [referring here to the sequence of B. licheniformis alpha-amylase (SEQ ID NO: 2)]:

Q9K,L,E; F11R,K,E; E12Q; D100N,L; V101H,R,K,D,E,F; V102A,T; I103H,K; N104R,K,D; H105R,K,D,E,W,F; L196R,K,D,E,F,Y; I212R,K,D,E; L230H,K,I; A232G,H,F,S,V; V233D; K234L,E; I236R,K,N,H,D,E; L241R,K,D,E,F; A260S; W263H; Q264R,D,K,E; N265K,R,D; A269R,K,D,E; L270R,K,H,D,E; V283H,D; F284H; D285N,L; V286R,K,H,D,E; Y290R,E; V312R,K,D,E; F323H; D325N; N326K,H,D,L; H327Q,N,E,D,F; Q330L,E; G332D; Q333R,K,H,E,L; S334A,V,T,L,I,D; L335G,A,S,T,N; E336R+R375E; T337D,K; T338D,E; T339D; Q360K,R,E; D365N; G371D,R.

Increased Stability at Low (Acidic) pH

In the context of the present invention, mutations (amino acid substitutions) of importance with respect to achieving increased stability at low pH appear to include mutations corresponding to the following mutations in the B. licheniformis alpha-amylase having the amino acid sequence shown in SEQ ID NO: 2:

mutations at positions H68, H91, H247, R305, K306, H382, K389, H405, H406, H450 or R483; the mutations:
H140Y;
H142Y;
H156Y;
H159Y;
H140D+H142R;
H140K+H142D; or
H142Y+H156Y as well as combinations of any two or more of these mutations.

Increased Thermostability and/or Altered Temperature Optimum (Altered Temperature/Activity Profile)

A further aspect of the invention relates to a variant of a parent Termamyl-like alpha-amylase, which variant is the result of one or more amino acid residues having been deleted from, substituted in or added to the parent alpha-amylase so as to achieve increased thermostability of the variant.

In may be mentioned that in relation to achieving increased thermostability, WO 96/23874 discloses that a particularly interesting variant of a Termamyl-like alpha-amylase comprises a mutation corresponding to one of the following mutations (using the numbering of the B. licheniformis alpha-amylase amino acid sequence shown in SEQ ID NO: 2):

L61W,V,F;
Y62W;
F67W;
K106R,F,W;
G145F,W
I212F,L,W,Y,R,K;
S151 replaced with any other amino acid residue and in particular with F,W,I or L;
R214W;
Y150R,K;
F143W; and/or
R146W.

WO 96/23874 further discloses in this connection that the mutations corresponding to one or more of the following mutations in the B. licheniformis alpha-amylase having the amino acid sequence shown in SEQ ID NO: 2 are of interest in relation to achieving increased thermostability relative to that of the parent alpha-amylase:

L241I,F,Y,W; and/or
I236L,F,Y,W
L7F,I,W
V259F,I,L
F284W
F350W
F343W
L427F,L,W
V481,F,I,L,W.

In the context of the present invention, it can be seen from an alignment of the amino acid sequences of alpha-amylases from various Bacillus species that B. licheniformis alpha-amylase and B. amyloliquefaciens alpha-amylase both contain an "insertion" of three amino acids relative to, e.g., B. stearothermophilus alpha-amylase.

From a model of the structure of B. licheniformis alpha-amylase built on the basis of the three-dimensional structure of the Termamyl-like alpha-amylase disclosed in WO 96/23784 (vide supra), taking into account the homology of B. licheniformis alpha-amylase to the Termamyl-like alpha-amylase in question, it can be seen that the above-mentioned "insertion" lies within a part of the structure denoted "loop 8" in WO 96/23784, making this loop bulkier in B. licheniformis alpha-amylase than in the Termamyl-like alpha-amylase and resulting in a loop that protrudes from the structure, thereby possibly destabilizing the structure. It is therefore contemplated that deletion of one or more amino acids in the region in question in B. licheniformis or B. amyloliquefaciens alpha-amylase will improve the thermostability of these alpha-amylases.

Especially interesting in this connection is deletion of three amino acids within the partial sequence from T369 to I377 (referring to the amino acid sequence of B. licheniformis alpha-amylase shown in SEQ ID NO: 2), i.e., the partial sequence: T369-K370-G371-D372-S373-Q374-R375-E376-I377 (or the corresponding partial sequence in B. amyloliquefaciens alpha-amylase). In addition to such deletions, substitution of one or more of the undeleted amino acids within the latter partial sequence may also be advantageous.

Preferable deletions of three amino acids in the partial sequence from T369 to I377 (in the *B. licheniformis* alpha-amylase) are deletion of K370+G371+D372 (i.e., K370*+G371*+D372*) or deletion of D372+S373+Q374 (i.e., D372*+S373*+Q374*) (or equivalent deletions in the corresponding partial sequence in *B. amyloliquefaciens* alpha-amylase).

Another type of mutation which would appear to be of value in improving the thermostability of these alpha-amylases is the substitution (replacement) of the entire partial amino acid sequence from T369 to I377 (referring to the sequence of the *B. licheniformis* alpha-amylase) with one of the following partial sequences of six amino acids (sequence numbering increasing from left to right): I-P-T-H-S-V; I-P-T-H-G-V; and I-P-Q-Y-N-I (or one of the same substitutions of the corresponding partial sequence in *B. amyloliquefaciens* alpha-amylase).

Other mutations which can apparently be of some importance in relation to achieving increased thermostability include amino acid substitutions at the following positions (referring to SEQ ID NO: 2):

R169 (e.g., R169I,L,F,T);
R173 (especially R173I,L,F,T);
I201F;
I212F;
A209L,T; or
V208I as well as combinations of any two or more of these mutations.

Increased Thermostability at Acidic pH and/or at Low $Ca^{2+}$ Concentration

In the context of the invention, mutations which appear to be of particular relevance in relation to obtaining variants according to the invention having increased thermostability at acidic pH (pH<7) and/or at low $Ca^{2+}$ concentration include mutations at the following positions (relative to *B. licheniformis* alpha-amylase, SEQ ID NO: 2):

H156, N172, A181, N188, N190, H205, D207, A209, A210, E211, Q264, N265

It may be mentioned here that N and E amino acid residues, respectively, at positions corresponding to N109 and E211, respectively, in SEQ ID NO: 2 constitute amino acid residues which are conserved in numerous Termamyl-like alpha-amylases. Thus, for example, the corresponding positions of these residues in the amino acid sequences of a number of Termamyl-like alpha-amylases which have already been mentioned (vide supra) are as follows:

| Termamyl-like alpha-amylase | N position | E position |
|---|---|---|
| *B. licheniformis* (SEQ ID NO: 2) | N190 | E211 |
| *B. amyloliquefaciens* (SEQ ID NO: 4) | N190 | E211 |
| *B. stearothermophilus* (SEQ ID NO: 6) | N193 | E210 |
| *Bacillus* NCIB 12512 (WO 95/26397) | N195 | E212 |
| *Bacillus* NCIB 12513 (WO 95/26397) | N195 | E212 |
| "*Bacillus* sp. #707" (Tsukamoto et al.) | N195 | E212 |

Mutations of these conserved amino acid residues appear to be very important in relation to improving thermostability at acidic pH and/or at low calcium concentration, and the following mutations are of particular interest in this connection (with reference to the numbering of the *B. licheniformis* amino acid sequence shown in SEQ ID NO: 2):

H156Y,D
N172R,H,K
A181T
N188P
N190L,F
H205C
D207Y
A209L,T,V
A210S
E211Q
Q264A,E,L,K,S,T
N265A,S,T,Y as well as any combination of two or more of these mutations.

An example of a particularly interesting double mutation in this connection is Q264S+N265Y.

Altered Cleavage Pattern

In the starch liquefaction process it is desirable to use an alpha-amylase which is capable of degrading the starch molecules into long, branched oligosaccharides, rather than an alpha-amylase which gives rise to formation of shorter, branched oligosaccharides (like conventional Termamyl-like alpha-amylases). Short, branched oligosaccharides (panose precursors) are not hydrolyzed satisfactorily by pullulanases, which are used after alpha-amylase treatment in the liquefaction process, but before addition of a saccharifying amyloglucosidase (glucoamylase). Thus, in the presence of panose precursors, the product mixture present after the glucoamylase treatment contains a significant proportion of short, branched, so-called limit-dextrin, viz. the trisaccharide panose. The presence of panose lowers the saccharification yield significantly and is thus undesirable.

Thus, one aim of the present invention is to arrive at a mutant alpha-amylase having appropriately modified starch-degradation characteristics but retaining the thermostability of the parent Termamyl-like alpha-amylase.

It may be mentioned here that according to WO 96/23874, variants comprising at least one of the following mutations are expected to prevent cleavage close to the branching point:

V54L,I,F,Y,W,R,K,H,E,Q
D53L,I,F,Y,W
Y56W
Q333W
G57 all possible amino acid residues
A52 amino acid residues larger than A, e.g., A52W,Y,L,F,I.

Increased Specific Activity

In a further aspect of the present invention, important mutations with respect to obtaining variants exhibiting increased specific activity appear to include mutations corresponding to the following mutations in the *B. licheniformis* alpha-amylase having the amino acid sequence shown in SEQ ID NO: 2:

mutations (amino acid substitutions) at positions S187 (especially S187D) or Q264 (e.g., Q264R,K,S);
mutations (substitutions) at position Y290 (especially Y290E,K);
the mutation V54I;
as well as combinations of any two or more of the latter mutations, or combinations of one, two or more of the latter mutations with the following multiple mutations: A1*+N2*+L3V+M15T+R23K+S29A+A30E+Y31H+A33S+E34D+H35I General Mutations in Variants of the Invention It may be preferred that a variant of the invention comprises one or more modifications in addition to those outlined above. Thus, it may be advantageous that one or more proline residues present in the part of the alpha-amylase variant which is modified is/are replaced with a non-proline residue which may be any of the possible, naturally occurring non-proline residues, and which preferably is an alanine, glycine, serine, threonine, valine or leucine.

Analogously, it may be preferred that one or more cysteine residues present among the amino acid residues with which the parent alpha-amylase is modified is/are replaced with a non-cysteine residue such as serine, alanine, threonine, glycine, valine or leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO: 2 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 2 by an Arg.

It will be understood that the present invention encompasses variants incorporating two or more of the above outlined modifications.

Furthermore, it may be advantageous to introduce point-mutations in any of the variants described herein.

Methods for Preparing Alpha-Amylase Variants

Several methods for introducing mutations into genes are known in the art. After a brief discussion of the cloning of alpha-amylase-encoding DNA sequences, methods for generating mutations at specific sites within the alpha-amylase-encoding sequence will be discussed.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labelled oligonucleotide probes may be synthesized and used to identify alpha-amylase-encoding clones from a genomic library prepared from the organism in question. Alternatively, a labelled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by Beaucage and Caruthers (1981) or the method described by Matthes et al. (1984). In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or Saiki et al. (1988).

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localized or region-specific random mutagenesis in at least three parts of the gene translating to the amino acid sequence in question, or within the whole gene.

WO 96/23874 discloses that in connection with achieving improved binding of a substrate (i.e., improved binding of a carbohydrate species, such as amylose or amylopectin) by a Termamyl-like alpha-amylase variant, modified (e.g., higher) substrate specificity and/or modified (e.g., higher) specificity with respect to cleavage (hydrolysis) of substrate, the following codon positions for the amino acid sequence shown in SEQ ID NO: 2 (or equivalent codon positions for another parent Termamyl-like alpha-amylase in the context of the invention) appear to be particularly appropriate for targeting:

13-18
50-56
70-76
102-109
163-172
189-199
229-235
360-364
327-335

Improvement of Liquefaction Performance at Low pH and Low Calcium Ion Concentration For an alpha-amylase to be used in a starch liquefaction process it is of particular interest that it be thermostable and able to function at low pH and low calcium concentrations. In order to improve these properties of a parent Termamyl-like alpha-amylase, in particular the *B. licheniformis* alpha-amylase or a variant or hybrid thereof, random mutagenesis (preferably by use of doped or spiked oligonucleotide primers) followed by appropriate selection of the resulting mutated enzymes may be performed. The direction of selection of regions to randomize and selection of doping are based primarily on stabilization of calcium ions already present, and on improvement in residue/residue or domain/domain electrostatic interactions at low pH. In addition, the regions which have been shown to include positions important for achieving good starch liquefaction performance may be selected.

In order to prepare a variant of a parent Termamyl-like alpha-amylase having the above properties, at least one of the following regions may advantageously be subjected to random mutagenesis (the numbering of the amino acid residues being as in SEQ ID NO: 2):

| Region | Residue | Description |
|--------|---------|-------------|
| I: | 153-163 | Calcium region between domain A & B, also containing H156 |
| II: | 178-192 | Calcium region between domain A & B |
| III: | 193-214 | Calcium region between domain A & B, also containing A209 |
| IV: | 232-237 | Calcium region between domain A & B |
| V: | 297-308 | Calcium region between domain A & C |
| VI: | 403-409 | Calcium region between domain A & C |
| VII: | 428-435 | Calcium region between domain A & C |
| VIII: | 131-136 | Region containing H133 |
| IX: | 164-175 | Region in contact with H133 region |
| X: | 262-278 | Region containing Q264 |

Preferably, two, three or four of the above regions are subjected to random mutagenesis in the construction of a novel alpha-amylase variant of the invention. For instance, the following combinations of regions are suitably subjected to random mutagenesis:
VIII+IX
VIII+IX+II
II+III+IV
IV+I Furthermore, it is preferred that the mutagenesis is carried out by use of doped or spiked oligonucleotides. The doping is preferably done so as to introduce amino acids contributing to improved stability at low pH and reduced calcium dependency at low pH of the resulting alpha-amylase variant. Furthermore, when selecting the doping scheme, the possibility of introducing Asn and Gln residues should generally be avoided, since Asn and Gln residues in general are associated with instability at low pH. Preferably, when a Pro residue can be inserted with potential benefits (e.g., as assessed from protein-structural considerations), the doping scheme is prepared to include a preference for introduction of a Pro residue.

The parent Termamyl-like alpha-amylase to be subjected to random mutagenesis according to the above principle may be any wild type alpha-amylase or a variant thereof containing one or more mutations. The parent may be a hybrid between at least two alpha-amylases as explained in further detail herein. Preferably, the parent alpha-amylase is a mutant of the *B. licheniformis* alpha-amylase having the sequence shown in SEQ ID NO: 2 containing at least one mutation, and preferably multiple mutations. The parent alpha-amylase may alternatively be a hybrid alpha-amylase which contains at least a part of the *B. licheniformis* (SEQ ID NO: 2) alpha-amylase. Specific examples of parent alpha-amylases suited to mutagenesis according to the above-described principles include: variants of the *B. licheniformis* (SEQ ID NO: 2) alpha-amylase which contain at least one of, i.e., one, two, three, four or all five of, the mutations H156Y, A181T, N190F, A209V and Q264S; hybrid alpha-amylases which contain a part of the *B. licheniformis* (SEQ ID NO: 2) alpha-amylase, preferably a C-terminal part thereof, such as amino acids 35-483 thereof, and a part of another Termamyl-like alpha-amylase such as *B. amyloliquefaciens* (SEQ ID NO: 4) alpha-amylase, preferably an N-terminal part thereof such as the first 38 amino acid residues thereof.

In relation to the above, a further aspect of the present invention relates to a method for generating a variant of a parent Termamyl-like alpha-amylase, which variant exhibits increased stability at low pH and at low calcium concentration relative to the parent, the method comprising:

(a) subjecting a DNA sequence encoding the parent Termamyl-like alpha-amylase to random mutagenesis, (b) expressing the mutated DNA sequence obtained in step (a) in a host cell, and (c) screening for host cells expressing a mutated alpha-amylase which has increased stability at low pH and low calcium concentration relative to the parent alpha-amylase.

Step (a) of the latter method of the invention is preferably performed using doped primers, as described in the working examples herein (vide infra).

Method of Performing Random Mutagenesis

The random mutagenesis of a DNA sequence encoding a parent alpha-amylase to be performed in accordance with step a) of the above-described method of the invention may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the amylolytic enzyme by any published technique, using, e.g., PCR, LCR or any DNA polymerase and ligase.

Preferably, the doping is carried out using "constant random doping", in which the percentage of wild-type and mutation in each position is predefined. Furthermore, the doping may be directed to have a preference for the introduction of certain nucleotides, and thereby a preference for introduction of one or more specific amino acid residues. The doping may, e.g., be made so as to allow for the introduction of 90% wild type and 10% mutations in each position. An additional consideration in choice of doping scheme is genetic as well as protein-structural constraints. The doping scheme may be made by using the DOPE program (see the working examples herein) which, inter alia, ensures that introduction of stop codons is avoided.

When PCR-generated mutagenesis is used, either a chemically treated or non-treated gene encoding a parent alpha-amylase enzyme is subjected to PCR under conditions that increase the misincorporation of nucleotides (Deshler (1992); Leung et al., 1989, *Technique* 1: 11-15).

A mutator strain of *E. coli* (Fowler et al., 1974, *Molec. Gen. Genet.* 133: 179-191), *S. cereviseae* or any other microbial organism may be used for the random mutagenesis of the DNA encoding the amylolytic enzyme by, e.g., transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent amylolytic enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step (b) or the screening step (c) being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis:

the random mutagenesis may advantageously be localized to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above, or any other suitable technique known in the art.

Alternatively, the DNA sequence encoding the part of the DNA sequence to be modified may be isolated, e.g., by being inserted into a suitable vector, and said part may subsequently be subjected to mutagenesis by use of any of the mutagenesis methods discussed above.

With respect to the screening step in the above-mentioned method of the invention, this may conveniently performed by use of an assay as described in connection with Example 2.

With regard to screening in general, a filter assay based on the following is generally applicable:

A microorganism capable of expressing the mutated amylolytic enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter, e.g., nylon or nitrocellulose. The top filter carrying the colonies of the expression organism may be any filter that has no or low affinity for binding proteins, e.g., cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatine, polyacrylamide, starch, filter paper, cloth; or any combination of immobilizing agents.

Alpha-amylase activity is detected by Cibacron Red labelled amylopectin, which is immobilized on agarose. For screening for variants with increased thermal and high-pH stability, the filter with bound alpha-amylase variants is incubated in a buffer at pH 10.5 and 60 or 65° C. for a specified time, rinsed briefly in deionized water and placed on the amylopectin-agarose matrix for activity detection. Residual activity is seen as lysis of Cibacron Red by amylopectin degradation. The conditions are chosen to be such that activity due to the alpha-amylase having the amino acid sequence shown in SEQ ID NO: 2 can barely be detected. Stabilized variants show, under the same conditions, increased colour intensity due to increased liberation of Cibacron Red.

For screening for variants with an activity optimum at a lower temperature and/or over a broader temperature range, the filter with bound variants is placed directly on the amylopectin-Cibacron Red substrate plate and incubated at the desired temperature (e.g., 4° C., 10° C. or 30° C.) for a specified time. After this time activity due to the alpha-amylase having the amino acid sequence shown in SEQ ID NO: 2 can barely be detected, whereas variants with optimum activity at a lower temperature will show increase amylopectin lysis. Prior to incubation onto the amylopectin matrix, incubation in all kinds of desired media—e.g., solutions containing $Ca^{2+}$, detergents, EDTA or other relevant additives—can be carried out in order to screen for changed dependency or for reaction of the variants in question with such additives.

Testing of Variants of the Invention

The testing of variants of the invention may suitably be performed by determining the starch-degrading activity of the variant, for instance by growing host cells transformed with a DNA sequence encoding a variant on a starch-containing agarose plate and identifying starch-degrading host cells. Further testing as to altered properties (including specific activity, substrate specificity, cleavage pattern, thermoactivation, pH optimum, pH dependency, temperature optimum, and any other parameter) may be performed in accordance with methods known in the art.

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favourably be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The alpha-amylase variants of this invention possess valuable properties allowing for a variety of industrial applications. In particular, enzyme variants of the invention are applicable as a component in washing, dishwashing and hard-surface cleaning detergent compositions. Numerous variants are particularly useful in the production of sweeteners and ethanol from starch, and/or for textile desizing. Conditions for conventional starch-conversion processes, including starch liquefaction and/or saccharification processes, are described in, e.g., U.S. Pat. No. 3,912,590 and in EP patent publications nos. 252,730 and 63,909.

Production of Sweeteners from Starch:

A "traditional" process for conversion of starch to fructose syrups normally consists of three consecutive enzymatic processes, viz. a liquefaction process followed by a saccharification process and an isomerization process. During the liquefaction process, starch is degraded to dextrins by an alpha-amylase (e.g., Termamyl™) at pH values between 5.5 and 6.2 and at temperatures of 95-160° C. for a period of approximately 2 hours. In order to ensure an optimal enzyme stability under these conditions, 1 mM of calcium is added (40 ppm free calcium ions).

After the liquefaction process the dextrins are converted into dextrose by addition of a glucoamylase (e.g., AMG™) and a debranching enzyme, such as an isoamylase or a pullulanase (e.g., Promozyme™). Before this step the pH is reduced to a value below 4.5, maintaining the high temperature (above 95° C.), and the liquefying alpha-amylase activity is denatured. The temperature is lowered to 60° C., and glucoamylase and debranching enzyme are added. The saccharification process proceeds for 24-72 hours.

After the saccharification process the pH is increased to a value in the range of 6-8, preferably pH 7.5, and the calcium is removed by ion exchange. The dextrose syrup is then converted into high fructose syrup using, e.g., an immmobilized glucoseisomerase (such as Sweetzyme™).

At least 3 enzymatic improvements of this process could be envisaged. All three improvements could be seen as individual benefits, but any combination (e.g., 1+2, 1+3, 2+3 or 1+2+3) could be employed:

Improvement 1. Reduction of the Calcium Dependency of the Liquefying Alpha-Amylase Addition of free calcium is required to ensure adequately high stability of the alpha-amylase, but free calcium strongly inhibits the activity of the glucose isomerase and needs to be removed, by means of an expensive unit operation, to an extent which reduces the level of free calcium to below 3-5 ppm. Cost savings could be obtained if such an operation could be avoided and the liquefaction process could be performed without addition of free calcium ions.

To achieve that, a less calcium-dependent Termamyl-like alpha-amylase which is stable and highly active at low concentrations of free calcium (<40 ppm) is required. Such a Termamyl-like alpha-amylase should have a pH optimum at a pH in the range of 4.5-6.5, preferably in the range of 4.5-5.5.

Improvement 2. Reduction of Formation of Unwanted Maillard Products

The extent of formation of unwanted Maillard products during the liquefaction process is dependent on the pH. Low pH favours reduced formation of Maillard products. It would thus be desirable to be able to lower the process pH from around pH 6.0 to a value around pH 4.5; unfortunately, all commonly known, thermostable Termamyl-like alpha-amylases are not very stable at low pH (i.e., pH<6.0) and their specific activity is generally low.

Achievement of the above-mentioned goal requires a Termamyl-like alpha-amylase which is stable at low pH in the range of 4.5-5.5 and at free calcium concentrations in the range of 0-40 ppm, and which maintains a high specific activity.

Improvement 3

It has been reported previously (U.S. Pat. No. 5,234,823) that when saccharifying with *A. niger* glucoamylase and *B. acidopullulyticus* pullulanase, the presence of residual alpha-amylase activity from the liquefaction process can lead to lower yields of dextrose if the alpha-amylase is not inactivated before the saccharification stage. This inactivation can typically be carried out by adjusting the pH to below 4.3 at 95° C., before lowering the temperature to 60° C. for saccharification.

The reason for this negative effect on dextrose yield is not fully understood, but it is assumed that the liquefying alpha-amylase (for example Termamyl™ 120 L from *B. licheniformis*) generates "limit dextrins" (which are poor substrates for *B. acidopullulyticus* pullulanase) by hydrolyzing 1,4-alpha-glucosidic linkages close to and on both sides of the branching points in amylopectin. Hydrolysis of these limit dextrins by glucoamylase leads to a build-up of the trisaccharide panose, which is only slowly hydrolyzed by glucoamylase.

The development of a thermostable alpha-amylase which does not suffer from this disadvantage would be a significant process improvement, as no separate inactivation step would be required.

If a Termamyl-like, low-pH-stable alpha-amylase is developed, an alteration of the specificity could be an advantage needed in combination with increased stability at low pH.

The methodology and principles of the present invention make it possible to design and produce variants according to the invention having required properties as outlined above. In this connection, particularly interesting mutations are mutations in a Termamyl-like alpha-amylase [for example Termamyl™ itself (*B. licheniformis* alpha-amylase; SEQ ID NO: 2); or a Termamyl-like alpha-amylase having an N-terminal amino acid sequence (i.e., the partial sequence up to the amino acid position corresponding to position 35 in Termamyl™) which is identical to that in *B. amyloliquefaciens* alpha-amylase (SEQ ID NO: 4), i.e., a Termamyl-like alpha-amylase having the following N-terminal sequence relative to amino acid sequence of Termamyl™:
A1*+N2*+L3V+M15T+R23K+S29A+A30E+Y31H+ A33S+E34D+H35I, where an asterisk (*) indicates deletion of the amino acid residue in question] at positions corresponding to any of the following positions in Termamyl™:
H133
H156
A181
A209
G310
H450
V128
N104
V54
S187
H293
A294
(where each of the latter amino acid residues may be replaced by any other amino acid residue, i.e., any other residue chosen among A, R, N, D, C, Q, E, G, H, I, L, K, M, F, P, S, T, W, Y and V), as well as the following triple deletions:
K370*+G371*+D372*
D372*+S373*+Q374*

Particularly preferred substitutions at the above-indicated positions are the following:
H133I
H156Y
A181T
A209V
G310D
H450Y
V128E
N104D
V54W,Y,F,I,L
S187D
H293Y
A294V.

Any combination of one or more (i.e., one, two, three, four, etc.) of the above indicated mutations may appropriately be effected in a Termamyl-like alpha-amylase in the context in question, and particularly interesting variants of the invention in the context of achieving one or more of the above-mentioned improvements in relation to the starch liquefaction behavior of alpha-amylases include variants comprising combinations of multiple mutations corresponding to the following combinations of mutations in Termamyl™ (SEQ ID NO: 2) itself:
V54W+N104D+V128E+H133I+H156Y+A181T+S187D+ A209V+H293Y+A294V+G310D+K370*+G371*+D372*+ H450Y;
V54W+N104D+V128E+H133I+H156Y+A181T+S187D+ A209V+H293Y+A294V+G310D+D372*+S373*+Q374*+ H450Y+;
V54Y+N104D+V128E+H133I+H156Y+A181T+S187D+ A209V+H293Y+A294V+G310D+K370*+G371*+D372*+ H450Y;
V54Y+N104D+V128E+H133I+H156Y+A181T+S187D+ A209V+H293Y+A294V+G310D+D372*+S373*+Q374*+ H450Y;
V54F+N104D+V128E+H133I+H156Y+A181T+S187D+ A209V+H293Y+A294V+G310D+K370*+G371*+D372*+ H450Y;
V54F+N104D+V128E+H133I+H156Y+A181T+S187D+ A209V+H293Y+A294V+G310D+D372*+S373*+Q374*+ H450Y;
V54I+N104D+V128E+H133I+H156Y+A181T+S187D+ A209V+H293Y+A294V+G310D+K370*+G371*+D372*+ H450Y;
V54I+N104D+V128E+H133I+H156Y+A181T+S187D+ A209V+H293Y+A294V+G310D+D372*+S373*+Q374*+ H450Y;
V54L+N104D+V128E+H133I+H156Y+A181T+S187D+ A209V+H293Y+A294V+G310D+K370*+G371*+D372*+ H450Y;
V54L+N104D+V128E+H133I+H156Y+A181T+S187D+ A209V+H293Y+A294V+G310D+D372*+S373*+Q374*+ H450Y.

Further interesting variants of the invention in this context include variants comprising single or multiple mutations corresponding to the following single or multiple mutations in Termamyl™ itself:
mutations (amino acid substitutions) at positions N172 (e.g., N172R,K), S187 (e.g., S187D), N188 (e.g., N188P), N190 (e.g., N190L,F), H205 (e.g., H205C), D207 (e.g., D207Y), A210 (e.g., A210S), Q264 (e.g., Q264S) or N265 (e.g., N265Y);
the following multiple mutations:
H156Y+A181T+A209V;
H156Y+A181T+N190F+A209V+Q264S;
A1*+N2*+L3V+M15T+R23K+S29A+A30E+Y31H+ A33S+E34D+H35I+H156Y+A181 T+A209V;
A1*+N2*+L3V+M15T+R23K+S29A+A30E+Y31H+ A33S+E34D+H35I+H156Y+A181T+N190F+A209V; or
A1*+N2*+L3V+M15T+R23K+S29A+A30E+Y31H+ A33S+E34D+H35I+H156Y+A181T+N190F+A209V+ Q264S
as well as combinations of any two or more of the latter single or multiple mutations.

As already indicated, numerous variants according to the invention are particularly well suited for use in starch conversion, e.g., in starch liquefaction. In this connection, a further aspect of the present invention relates to compositions comprising a mixture of:

(i) the alpha-amylase from *B. licheniformis* having the sequence shown in SEQ ID NO: 2 with one or more variants (mutant alpha-amylases) according to the invention derived from (as the parent Termamyl-like alpha-amylase) the *B. stearothermophilus* alpha-amylase having the sequence shown in SEQ ID NO: 6; or (ii) the alpha-amylase from *B. stearothermophilus* having the sequence shown in SEQ ID NO: 6 with one or more variants (mutant alpha-amylases) according to the invention derived from one or more other parent Termamyl-like alpha-amylases (e.g., from the *B. licheniformis* alpha-amylase having the sequence shown in SEQ ID NO: 2, or from one of the other parent Termamyl-like alpha-amylases specifically referred to herein); or (iii) one or more variants (mutant alpha-amylases) according to the invention derived from (as the parent Termamyl-like alpha-amylase) the *B. stearothermophilus* alpha-amylase having the sequence shown in SEQ ID NO: 6 with one or more variants (mutant alpha-amylases) according to the invention derived from one or more other parent Termamyl-like alpha-amylases (e.g., from the *B. licheniformis* alpha-amylase having the sequence shown in SEQ ID NO: 2, or from one of the other parent Termamyl-like alpha-amylases specifically referred to herein).

Preferred mutations in a variant of *B. stearothermophilus* alpha-amylase to be incorporated in such a mixture include substitutions at N193 and/or at E210, and/or the pairwise deletions R179*+G180* or I181*+G182* (using the numbering of the amino acid sequence for this particular alpha-amylase).

Compositions of one of the latter types, containing *B. stearothermophilus* alpha-amylase or a variant thereof according to the invention, appear to have great potential for use in starch liquefaction. The ratio (expressed, e.g., in terms of mg of active amylolytic protein per liter of liquid medium) between the individual alpha-amylolytic components of a given mixture will depend on the exact nature and properties of each component.

Detergent Compositions

As mentioned above, variants of the invention may suitably be incorporated in detergent compositions. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising a variant of the invention may additionally comprise one or more other enzymes, such as a lipase, cutinase, protease, cellulase, peroxidase or laccase, and/or another alpha-amylase.

Alpha-amylase variants of the invention may be incorporated in detergents at conventionally employed concentrations. It is at present contemplated that a variant of the invention may be incorporated in an amount corresponding to 0.00001-1 mg (calculated as pure, active enzyme protein) of alpha-amylase per liter of wash/dishwash liquor using conventional dosing levels of detergent.

Materials and Methods
Construction of pSNK101

This *E. coli/Bacillus* shuttle vector can be used to introduce mutations without expression of alpha-amylase in *E. coli* and then be modified in such way that the alpha-amylase is active in *Bacillus*. The vector was constructed as follows: The alpha-amylase gene in the pX vector (pDN1528 with the following alterations within amyL: BAN(1-33), H156Y, A181T, N190F, A209V, Q264S, the plasmid pDN1528 is further described in Example 1) was inactivated by interruption in the PstI site in the 5' coding region of the alpha-amylase gene by a 1.2 kb fragment containing an *E. coli* origin fragment. This fragment was amplified from the pUC19 (GenBank Accession #:X02514) using the forward primer: 5'-gacctgcagtcaggcaacta-3' (SEQ ID NO: 8) and the reverse primer: 5'-tagagtcgacctgcaggcat-3' (SEQ ID NO: 9). The PCR amplicon and the pX plasmid containing the alpha-amylase gene were digested with PstI at 37° C. for 2 hrs. The pX vector fragment and the *E. coli* origin amplicon were ligated at room temperature for 1 hour and transformed in *E. coli* by electrotransformation. The resulting vector is designated pSnK101.

Fermentation and Purification of Alpha-Amylase Variants

A *B. subtilis* strain harbouring the relevant expression plasmid is streaked on an LB-agar plate with 15 micrograms/ml chloramphenicol from −80° C. stock, and grown overnight at 37° C.

The colonies are transferred to 100 ml BPX media supplemented with 15 micrograms/ml chloramphenicol in a 500 ml shaking flask.

Composition of BPX medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| Na$_2$HPO$_4$, 12 H$_2$O | 9 g/l |
| Pluronic ™ | 0.1 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM acetate pH 5.5. The UF-filtrate is applied on an S-sepharose F.F. and elution is carried out by step elution with 0.2 M NaCl in the same buffer. The eluate is dialyzed against 10 mM Tris, pH 9.0 and applied on a Q-sepharose F.F. and eluted with a linear gradient from 0-0.3 M NaCl over 6 column volumes. The fractions which contain the activity (measured by the Phadebas assay) are pooled, pH was adjusted to pH 7.5 and remaining color was removed by a treatment with 0.5% w/vol. active coal in 5 minutes.

Assay for Alpha-Amylase Activity

Alpha-amylase activity is determined by a method employing Phadebas® tablets as substrate. Phadebas tablets (Phadebas® Amylase Test, supplied by Pharmacia Diagnostic) contain a cross-linked insoluble blue-coloured starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM CaCl$_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

General Method for Random Mutagenesis by Use of the DOPE Program

The random mutagenesis may be carried out by the following steps:
1. Select regions of interest for modification in the parent enzyme
2. Decide on mutation sites and nonmutated sites in the selected region
3. Decide on which kind of mutations should be carried out, e.g., with respect to the desired stability and/or performance of the variant to be constructed
4. Select structurally reasonable mutations.
5. Adjust the residues selected by step 3 with regard to step 4.
6. Analyze by use of a suitable dope algorithm the nucleotide distribution.
7. If necessary, adjust the wanted residues to genetic code realism (e.g., taking into account constraints resulting from the genetic code (e.g., in order to avoid introduction of stop codons)) (the skilled person will be aware that some codon combinations cannot be used in practice and will need to be adapted)
8. Make primers
9. Perform random mutagenesis by use of the primers
10. Select resulting alpha-amylase variants by screening for the desired improved properties.

Suitable dope algorithms for use in step 6 are well known in the art. One algorithm is described by Tomandl et al., 1997, *Journal of Computer-Aided Molecular Design* 11: 29-38. Another algorithm, DOPE, is described in the following:

The Dope Program

The "DOPE" program is a computer algorithm useful to optimize the nucleotide composition of a codon triplet in such a way that it encodes an amino acid distribution which resembles most the wanted amino acid distribution. In order to assess which of the possible distributions is the most similar to the wanted amino acid distribution, a scoring function is needed. In the "Dope" program the following function was found to be suited:

$$s \equiv \prod_{i=1}^{N} \left( \frac{x_i^{y_i}(1-x_i)^{1-y_i}}{y_i^{y_i}(1-y_i)^{1-y_i}} \right)^{w_i},$$

where the $x_i$'s are the obtained amounts of amino acids and groups of amino acids as calculated by the program, $y_i$'s are the wanted amounts of amino acids and groups of amino acids as defined by the user of the program (e.g., specify which of the 20 amino acids or stop codons are wanted to be introduced, e.g., with a certain percentage (e.g., 90% Ala, 3% Ile, 7% Val), and $w_i$'s are assigned weight factors as defined by the user of the program (e.g., depending on the importance of having a specific amino acid residue inserted into the position in question). N is 21 plus the number of amino acid groups as defined by the user of the program. For purposes of this function $0^0$ is defined as being 1.

A Monte-Carlo algorithm (one example being the one described by Valleau, J. P. & Whittington, S. G. (1977) A guide to Mont Carlo for statistical mechanics: 1 Highways. In "Stastisical Mechanics, Part A" Equlibrium Techniqeues ed. B. J. Berne, New York: Plenum) is used for finding the maximum value of this function. In each iteration the following steps are performed:

1. A new random nucleotide composition is chosen for each base, where the absolute difference between the current and the new composition is smaller than or equal to d for each of the four nucleotides G,A,T,C in all three positions of the codon (see below for definition of d).
2. The scores of the new composition and the current composition are compared by the use of the function s as described above. If the new score is higher or equal to the score of the current composition, the new composition is kept and the current composition is changed to the new one. If the new score is smaller, the probability of keeping the new composition is exp(1000(new_score−current_score)).

A cycle normally consists of 1000 iterations as described above in which d is decreasing linearly from 1 to 0. One hundred or more cycles are performed in an optimization process. The nucleotide composition resulting in the highest score is finally presented.

Example 1

Construction of Termamyl™ Variants in Accordance with the Invention

Termamyl (*B. licheniformis* alpha-amylase SEQ ID NO: 2) is expressed in *B. subtilis* from a plasmid denoted pDN1528. This plasmid contains the complete gene encoding Termamyl, amyL, the expression of which is directed by its own promoter. Further, the plasmid contains the origin of replication, ori, from plasmid pUB110 and the cat gene from plasmid pC194 conferring resistance towards chloramphenicol. pDN1528 is shown in FIG. 9 of WO 96/23874.

A specific mutagenesis vector containing a major part of the coding region of SEQ ID NO: 1 was prepared. The important features of this vector, denoted pJeEN1, include an origin of replication derived from the pUC plasmids, the cat gene conferring resistance towards chloramphenicol, and a frameshift-containing version of the bla gene, the wild type of which normally confers resistance towards ampicillin ($amp^R$ phenotype). This mutated version results in an $amp^S$ phenotype. The plasmid pJeEN1 is shown in FIG. 10 of WO 96/23874, and the *E. coli* origin of replication, ori, bla, cat, the 5'-truncated version of the Termamyl amylase gene, and selected restriction sites are indicated on the plasmid.

Mutations are introduced in amyL by the method described by Deng and Nickoloff (1992, *Anal. Biochem.* 200: 81-88) except that plasmids with the "selection primer" (primer #6616; see below) incorporated are selected based on the $amp^R$ phenotype of transformed *E. coli* cells harboring a plasmid with a repaired bla gene, instead of employing the selection by restriction enzyme digestion outlined by Deng and Nickoloff. Chemicals and enzymes used for the mutagenesis were obtained from the Chameleon Ò mutagenesis kit from Stratagene (catalogue number 200509).

After verification of the DNA sequence in variant plasmids, the truncated gene, containing the desired alteration, is subcloned into pDN1528 as a PstI-EcoRI fragment and transformed into the protease- and amylase-depleted *Bacillus subtilis* strain SHA273 (described in WO 92/11357 and WO 95/10603) in order to express the variant enzyme.

The Termamyl variant V54W was constructed by the use of the following mutagenesis primer (written 5' to 3', left to right):

(SEQ ID NO: 10)
PG GTC GTA GGC ACC GTA GCC CCA ATC CGC TTG

The Termamyl variant A52W+V54W was constructed by the use of the following mutagenesis primers (written 5' to 3', left to right):

(SEQ ID NO: 11)
PG GTC GTA GGC ACC GTA GCC CCA ATC CCA TTG GCT CG

Primer #6616 (written 5' to 3', left to right; P denotes a 5' phosphate):

(SEQ ID NO: 12)
P CTG TGA CTG GTG AGT ACT CAA CCA AGT C

The Termamyl variant V54E was constructed by the use of the following mutagenesis primer (written 5'-3', left to right):

(SEQ ID NO: 13)
PGG TCG TAG GCA CCG TAG CCC TCA TCC GCT TG

The Termamyl variant V54M was constructed by the use of the following mutagenesis primer (written 5'-3', left to right):

(SEQ ID NO: 14)
PGG TCG TAG GCA CCG TAG CCC ATA TCC GCT TG

The Termamyl variant V54I was constructed by the use of the following mutagenesis primer (written 5'-3', left to right):

(SEQ ID NO: 15)
PGG TCG TAG GCA CCG TAG CCA ATA TCC GCT TG

The Termamyl variants Y290E and Y290K were constructed by the use of the following mutagenesis primer (written 5'-3', left to right):

(SEQ ID NO: 16)
PGC AGC ATG GAA CTG CTY ATG AAG AGG CAC GTC AAA C

Y represents an equal mixture of C and T. The presence of a codon encoding either glutamate or lysine in position 290 was verified by DNA sequencing.

The Termamyl variant N190F was constructed by the use of the following mutagenesis primer (written 5'-3', left to right):

(SEQ ID NO: 17)
PCA TAG TTG CCG AAT TCA TTG GAA ACT TCC C

The Termamyl variant N188P+N190F was constructed by the use of the following mutagenesis primer (written 5'-3', left to right):

(SEQ ID NO: 18)
PCA TAG TTG CCG AAT TCA GGG GAA ACT TCC CAA TC

The Termamyl variant H140K+H142D was constructed by the use of the following mutagenesis primer (written 5'-3', left to right):

(SEQ ID NO: 19)
PCC GCG CCC CGG GAA ATC AAA TTT TGT CCA GGC TTT AAT TAG

The Termamyl variant H156Y was constructed by the use of the following mutagenesis primer (written 5'-3', left to right):

(SEQ ID NO: 20)
PCA AAA TGG TAC CAA TAC CAC TTA AAA TCG CTG

The Termamyl variant A181T was constructed by the use of the following mutagenesis primer (written 5'-3', left to right):

(SEQ ID NO: 21)
PCT TCC CAA TCC CAA GTC TTC CCT TGA AAC

The Termamyl variant A209V was constructed by the use of the following mutagenesis primer (written 5'-3', left to right):

(SEQ ID NO: 22)
PCTT AAT TTC TGC TAC GAC GTC AGG ATG GTC ATA ATC

The Termamyl variant Q264S was constructed by the use of the following mutagenesis primer (written 5'-3', left to right):

(SEQ ID NO: 23)
PCG CCC AAG TCA TTC GAC CAG TAC TCA GCT ACC GTA AAC

The Termamyl variant S187D was constructed by the use of the following mutagenesis primer (written 5'-3', left to right):

(SEQ ID NO: 24)
PGC CGT TTT CAT TGT CGA CTT CCC AAT CCC

The Termamyl variant DELTA(K370-G371-D372) (i.e., deleted of amino acid residues nos. 370, 371 and 372) was constructed by the use of the following mutagenesis primer (written 5'-3', left to right):

(SEQ ID NO: 25)
PGG AAT TTC GCG CTG ACT AGT CCC GTA CAT ATC CCC

The Termamyl variant DELTA(D372-S373-Q374) was constructed by the use of the following mutagenesis primer (written 5'-3', left to right):

(SEQ ID NO: 26)
PGG CAG GAA TTT CGC GAC CTT TCG TCC CGT ACA TAT C

The Termamyl variants A181T and A209V were combined to A181T+A209V by digesting the A181T containing pDN1528-like plasmid (i.e., pDN1528 containing within amyL the mutation resulting in the A181T alteration) and the A209V-containing pDN1528-like plasmid (i.e., pDN1528 containing within amyL the mutation resulting in the A209V alteration) with restriction enzyme C/al which cuts the pDN1528-like plasmids twice resulting in a fragment of 1116 bp and the vector-part (i.e., contains the plasmid origin of replication) of 3850 bp. The fragment containing the A209V mutation and the vector part containing the A181T mutation were purified by QIAquick gel extraction kit (purchased from QIAGEN) after separation on an agarose gel. The fragment and the vector were ligated and transformed into the protease and amylase depleted *Bacillus subtilis* strain referred to above. Plasmid from amy+ (clearing zones on starch containing agar-plates) and chloramphenicol resistant transformants were analysed for the presence of both mutations on the plasmid.

In a similar way as described above, H156Y and A209V were combined utilizing restriction endonucleases Acc65I and EcoRI, giving H156Y+A209V.

H156Y+A209V and A181T+A209V were combined into H156Y+A181T+A209V by the use of restriction endonucleases Acc65I and HindIII.

The 35 N-terminal residues of the mature part of Termamyl variant H156Y+A181T+A209V were substituted by the 33 N-terminal residues of the *B. amyloliquefaciens* alpha-amylase (SEQ ID NO: 4) (which in the present context is termed BAN) to by a SOE-PCR approach (Higuchi et al., 1988, *Nucleic Acids Research* 16: 7351) as follows:

```
Primer 19364 (sequence 5'-3'):
                                    (SEQ ID NO: 27)
CCT CAT TCT GCA GCA GCA GCC GTA AAT GGC
ACG CTG Primer 19362:
                                    (SEQ ID NO: 28)
CCA GAC GGC AGT AAT ACC GAT ATC CGA TAA
ATG TTC CG Primer 19363:
                                    (SEQ ID NO: 29)
CGG ATA TCG GTA TTA CTG CCG TCT GGA TTC Primer 1C:
                                    (SEQ ID NO: 30)
CTC GTC CCA ATC GGT TCC GTC
```

A standard PCR, polymerase chain reaction, was carried out using the Pwo thermostable polymerase from Boehringer Mannheim according to the manufacturer's instructions and the temperature cycles: 5 minutes at 94° C., 25 cycles of (94° C. for 30 seconds, 50° C. for 45 seconds, 72° C. for 1 minute), 72° C. for 10 minutes.

An approximately 130 bp fragment was amplified in a first PCR denoted PCR1 with primers 19364 and 19362 on a DNA fragment containing the gene encoding the *B. amyloliquefaciens* alpha-amylase.

An approximately 400 bp fragment was amplified in another PCR denoted PCR2 with primers 19363 and 1C on template pDN1528.

PCR1 and PCR2 were purified from an agarose gel and used as templates in PCR3 with primers 19364 and 1C, which resulted in a fragment of approximately 520 bp. This fragment thus contains one part of DNA encoding the N-terminus from BAN fused to a part of DNA encoding Termamyl from the 35th amino acid.

The 520 bp fragment was subcloned into a pDN1528-like plasmid (containing the gene encoding Termamyl variant H156Y+A181T+A209V) by digestion with restriction endonucleases PstI and SacII, ligation and transformation of the *B. subtilis* strain as previously described. The DNA sequence between restriction sites PstI and SacII was verified by DNA sequencing in extracted plasmids from amy+ and chloramphenicol resistant transformants.

The final construct containing the correct N-terminus from BAN and H156Y+A181T+A209V was denoted BAN (1-35)+H156Y+A181T+A209V.

N190F was combined with BAN(1-35)+H156Y+A181T+ A209V giving BAN(1-35)+H156Y+A181T+N190F+ A209V by carrying out mutagenesis as described above except that the sequence of amyL in pJeEN1 was substituted by the DNA sequence encoding Termamyl variant BAN(1-35)+H156Y+A181T+A209V.

Q264S was combined with BAN(1-35)+H156Y+A181T+ A209V giving BAN(1-35)+H156Y+A181T+A209V+ Q264S by carrying out mutagenesis as described above except that the sequence of amyL in pJeEN was substituted by the DNA sequence encoding Termamyl variant BAN(1-35)+H156Y+A181T+A209V.

BAN(1-35)+H156Y+A181T+A209V+Q264S and BAN (1-35)+H156Y+A181T+N190F+A209V were combined into BAN(1-35)+H156Y+A181T+N190F+A209V+Q264S utilizing restriction endonucleases BsaHI (BsaHI site was introduced close to the A209V mutation) and PstI.

Example 2

Construction, by Localized Random, Doped Mutagenesis, of Termamyl-Like Alpha-Amylase Variants Having an Improved Stability at Low pH and a Reduced Dependency on Calcium Ions for Stability Compared to the Parent Enzyme Alpha-amylases are of great importance for the industrial starch liquefaction process. The variant of the thermostable *B. licheniformis* alpha-amylase consisting of amino acids 1-33 of the *B. amyloliquefaciens* amylase (SEQ ID NO: 4) fused to amino acids 36-483 of the *B. licheniformis* amylase (SEQ ID NO: 2) and further comprising the following mutations:

Y156, T181, F190, V209 and S264 (the construction of this variant is described in Example 1) has a very satisfactory stability at low pH and low calcium concentrations. In an attempt to further improve the stability at low pH and low calcium concentration of said alpha-amylase variant random mutagenesis in preselected regions was performed.

The regions were:
Region: Residue:
I: Phe153-Thr163
II: Gln178-Asn192
III: His205-Arg214
IV: Ala232-Asp237
and
VIII: Gly131-Lys136
IX: Asp164-Tyr175
X: Tyr 262-Thr278

| Region | Total % | Mean % | Number of residues changed |
|---|---|---|---|
| I: | 35 | 88 | 8 out of 11 |
| II: | 20 | 86 | 11 out of 15 |
| III: | 27 | 88 | 10 out of 10 |
| IV: | 34 | 91 | 11 out of 12 |
| VIII: | 39 | 86 | 6 out of 6 |
| IX: | 46 | 93 | 12 out of 12 |
| X: | 27 | 90 | 12 out of 13 |
| VIII + IX: | 18 | | |
| VIII + IX + II: | 4 | | |
| II + III + IV: | 2 | | |
| IV + I: | 12 | | |

The numbers under Total % give the total number of wild-type (wt) amino acids desired in a given region after doping. The number is obtained by multiplication of the number of mutated positions (e.g., 8 with respect to region I) by their respective wt. With respect to region I the desired total % is 80*80*90*90*90*90*95*90/100=35%.

The Mean % is the mean doping level for the total number of positions of the region in question (e.g., 11 positions with respect to region I). For region I the mean % is calculated as follows: 80+80+90+90+90+90+95+90=705 divided by 11=88%

The DOPE software (see Materials and Methods) was used to determine spiked codons for each suggested change in the seven regions minimizing the amount of stop codons. The exact distribution of nucleotides was calculated in the three positions of the codon to give the suggested population of amino acid changes. The doped regions were doped specifically in the indicated positions to have a high chance of getting the desired residues, but still allow other possibilities.

For instance, the original H156 in the wt sequence was mutated into a Y, meaning a new codon, and then doped 10% for other residues. That is the DNA sequence has the code for a Y instead for a H. In position 156 the Tyr has been programmed to be 90% desired and other residues has been freely allowed. For some positions it was not possible to create the suggested population of amino acid residues because the genetic code restricted the structurally and functionally desired residues. The resulting seven doped oligonucleotides are shown in tables 1-7: with the wt nucleotide and amino acid sequences and the distribution of nucleotides for each doped position. All library primers were synthesized as sense strands.

TABLE 1

Library DASI (Phe153-Thr163)

```
153 154 155 156 157 158 159 160 161 162 163
Phe Lys Trp Tyr Trp Tyr His Phe Asp Gly Thr

Primer: 5'-CGC GGC AGC ACA TAC AGC GAT T1T 2A3

TGG 45T TGG 67T 8AT TTT GAC GGA A9C GAT TGG GAC

GAG TCC CGA AAG-3'(SEQ ID NO: 31)
```

Distribution of nucleotides for each doped position.

1: 80% T, 20% A.
2: 96% A, 2% G, 2% C.
3: 98% A, 2% T.
4: 93% T, 4% G, 3% A.
5: 97% A, 3% G.
6: 98% T, 2% A.
7: 97% A, 3% C.
8: 90% C, 10% T.
9: 95% C, 5% A.

TABLE 2

Library DASII (Gln178-Asn192)

```
178 179 180 181 182 183 184 185 186 187 188
Gln Gly Lys Thr Trp Asp Trp Glu Val Ser Asn 189 190 191 192
Glu Phe Gly Asn

Primer: 5'-CTG AAC CGC ATC TAT AAG TTT 1A2
```

TABLE 2-continued

Library DASII (Gln178-Asn192)

```
34T AAG 567 TGG GAT 89G GA10 GTT A11T 1213T GAA

T1415 161718 AAC TAT GAT TAT TTG ATG TAT-3'

(SEQ ID NO: 32)
```

Distribution of nucleotides for each doped position.

1: 93% C, 7% A.
2: 84% G, 16% T.
3: 95% G, 5% A.
4: 95% G, 5% C.
5: 94% A, 6% G.
6: 95% C, 5% A.
7: 62% T, 38% G.
8: 87% T, 13% A.
9: 91% G, 9% C.
10: 92% G, 8% T.
11: 90% G, 5% A, 5% C.
12: 88% A, 12% C.
13: 88% A, 12% C.
14: 93% T, 5% A, 2% C.
15: 97% T, 3% G.
16: 86% G, 14% A.
17: 89% G, 11% C.
18: 60% G, 40% T.

TABLE 3

Library DASIII (His205-Arg214)

```
205 206 207 208 209 210 211 212 213 214
His Pro Asp Val Val Ala Glu Ile Lys Arg

Primer: 5'-TAT GCC GAC ATC GAT TAT GAC 12T

3CT 456 7TT 8910 1112T 13A14 15T16 A17A 1819A

TGG GGC ACT TGG TAT GCC AAT-3'

(SEQ ID NO: 33)
```

Distribution of nucleotides for each doped position.

1: 89% C, 11% T.
2: 89% A, 11% G.
3: 95% C, 2.5% T, 2.5% A.
4: 96% G, 1% A, 3% T.
5: 96% A, 4% C.
6: 98% T, 2% A.
7: 95% G, 2.5% A, 2.5% C.
8: 93% G, 7% A.
9: 96% T, 4% A.
10: 84% A, 16% G.
11: 81% G, 7% A, 7% T, 5% C.
12: 98% C, 2% A.
13: 96% G, 4% C.
14: 94% G, 6% T.
15: 82% A, 18% T.
16: 50% A, 50% T.
17: 90% A, 10% G.
18: 70% A, 30% C.
19: 86% G, 14% A

TABLE 4

Library DASIV (Ala232-Asp243)

232 233 234 235 236 237 238 239 240 241 242 243
Ala Val Lys His Ile Lys Phe Ser Phe Leu Arg Asp

Primer: 5'-TTG GAC GGT TTC CGT CTT GAT 12T

G3T AAA 456 7TT A8G T9T 1011T T12T 13T14 1516G

GA17 TGG GTT AAT CAT GTC AGG GAA-3'

(SEQ ID NO: 34)

Distribution of nucleotides for each doped position.
1: 93% G, 3.5% A, 3.5% T.
2: 94% C, 4% T.
3: 94% T, 6% C.
4: 93% C, 2% T, 2% A, 3% G.
5: 98% A, 2% T.
6: 98% T, 2% A.
7: 95% A, 5% C.
8: 94% A, 6% G.
9: 90% T, 10% A.
10: 89% T, 11% A.
11: 89% C, 11% A.
12: 95% T, 5% A
13: 64% C, 33% T, 3% A.
14: 93% A, 7% T.
15: 90% A, 10% C.
16: 90% G, 5% A, 5% C
17: 90% T, 10% A

TABLE 5

Library DASVIII (Gly131-Lys136)

131 132 133 134 135 136
Gly Glu His Leu Ile Lys

Primer: 5'-GCT GAC CGC AAC CGC GTA ATT

TCA 123 GA4 56T 78A 9TA A10G GCC TGG

ACA CAT TTT CAT TTT-3'(SEQ ID NO: 35)

Distribution of nucleotides for each doped position.
1: 91% G, 9% A.
2: 87% G, 13% C.
3: 90% T, 10% G.
4: 90% G, 10% T.
5: 85% C, 8% T, 7% A.
6: 89% A, 9% T, 2% C.
7: 88% T, 12% A
8: 88% T, 11% C, 1% G
9: 92% A, 8% T
10: 93% A, 7% G

TABLE 6

Library DASIX (Asp164-Tyr175)

164 165 166 167 168 169 170 171 172 173 174 175
Asp Trp Asp Glu Ser Arg Lys Leu Asn Arg Ile Tyr

Primer: 5'-TGG TAC CAT TTT GAC GGA ACC GAT

TGG 1A2 GAG 3CG CGA A4G 56A A7T A8G 9 1011

TABLE 6-continued

Library DASIX (Asp164-Tyr175)

T12T AAG TTT CAA GGA AAG GCT TGG-3'

(SEQ ID NO: 36)

Distribution of nucleotides for each doped position.
1: 94% G, 6% A.
2: 96% T, 4% G.
3: 92% T, 4% A, 4% G.
4: 95% A, 5% G.
5: 93% C, 7% A.
6: 92% T, 8% A.
7: 90% A, 5% G, 5% C.
8: 90% G, 10% A.
9: 92% A, 6% G, 2% T.
10: 92% T, 8% A.
11: 50% T, 50% C.
12: 96% A, 4% T.

TABLE 7

Library DASX (Tyr262-Asn278)

262 263 264 265 266 267 268 269 270 271 272 273
Tyr Trp Ser Asn Asp Leu Gly Ala Leu Glu Asn Tyr 374 275 276 277 278
Leu Asn Lys Thr Asn

Primer: 5'-GAA ATG TTT ACG GTA GCT GAA T1T TGG 234 56T 7A8 91011 1213T 1415T 16T17 GA18 A19T

T20T 21T22 A23C A24G ACA 25AT TTT AAT CAT TCA

GTG TTT GAC-3'

(SEQ ID NO: 37)

Distribution of nucleotides for each doped position.
1: 95% A, 5% T.
2: 97% A, 3% G.
3: 95% G, 2.5% A, 2.5% C.
4: 94% T, 6.2% G.
5: 97% A, 3% T.
6: 94% A, 3% G, 3% C.
7: 95% G, 5% A.
8: 95% T, 5% A.
9: 52% T, 45% C, 3% A.
10: 96% T, 4% C.
11: 60% A, 40% G.
12: 90% G, 10% A.
13: 94% G, 6% C.
14: 81% G, 8% A, 8% T, 3% C.
15: 98% C, 2% T.
16: 90% C, 10% A.
17: 50% G, 50% T.
18: 90% A, 10% T.
19: 90% A, 5% G, 5% C.
20: 95% A, 5% T.
21: 91% T, 9% A.
22: 92% A, 8% G.
23: 94% A, 3% G, 3% C.
24: 93% G, 7% A.
25: 90% A, 10% G.

Random Mutagenesis

The spiked oligonucleotides apparent from Tables 1-7 (which by a common term is designated FDAS in FIG. 3) and reverse primers RDAS for each region and specific *B. licheniformis* primers covering the SacII and the SalI sites are used to generate PCR-library-fragments by the overlap extension method (Horton et al., 1989, *Gene* 77: 61-68) with an overlap of 21 bp. FIG. 3 shows the PCR strategy. The PCR fragments are cloned in the *E. coli/Bacillus* shuttle vector pSNK101 (see Materials and Methods) enabling mutagenesis in *E. coli* and immediate expression in *Bacillus subtilis* preventing lethal accumulation of amylases in *E. coli*. After establishing the cloned PCR fragments in *E. coli*, a modified pUC19 fragment is digested out of the plasmid and the promoter and the mutated Termamyl gene is physically connected and expression can take place in *Bacillus*.

Screening

The seven libraries may be screened in the low pH and the low calcium filter assays described below.

Low pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 micrograms/ml chloramphenicol at 37° C. for at least 21 hrs. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with citrate buffer, pH 4.5 and incubated at 80° C. for 15 minutes. The cellulose acetate filters with colonies are stored on the TY-plates at room temperature until use. After incubation, residual activity is detected on plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are rescreened twice under the same conditions as the first screen.

Low Calcium Filter Assay

The assay is performed in the same way as the low pH filter assay with the following modifications: The filter with bound proteins is incubated at 95° C., pH 6.0 for 1 hour. with different EDTA concentrations (0.001 mM-100 mM).

The following variants were obtained by the above method (BAN designates *B. amyloliquefaciens* alpha-amylase):

*BAN/Termamyl hybrid*+H156Y+A181T+N190F+A209V+Q264S+E211Q

BAN/Termamyl Hybrid*+H156Y+A181T+N190F+A209V+Q264S+H205C+D207Y+A210S

The mutations indicated in bold were introduced by the random mutagenesis method. The stability data for these variants appear from Table 11 in Example 3.

In an analogous manner to that described above, random mutagenesis of the above identified seven regions are performed on the parent *B. licheniformis* alpha-amylase (SEQ ID NO: 2). The doping scheme is determined analogously to that used above.

Example 3

Measurement of the Calcium- and pH-Dependent Stability

Normally, the industrial liquefaction process runs using pH 6.0-6.2 as liquefaction pH and an addition of 40 ppm free calcium in order to improve the stability at 95-105° C. Some of the herein proposed substitutions have been made in order to improve the stability at 1. lower pH than pH 6.2 and/or
2. at free calcium levels lower than 40 ppm free calcium.

Three different methods have been used to measure the improvements in stability obtained by the different substitutions in Termamyl:

1. One assay which measures the stability at slightly reduced pH, pH 5.5, in the presence of 40 ppm free calcium. (thereby, the improvement of stability at low pH is measured). 10 micrograms of the variant were incubated under the following conditions: A 0.1 M acetate solution, pH adjusted to pH 5.5, containing 40 ppm calcium and 5% w/w common corn starch (free of calcium). Incubation was made in a water bath at 95° C. for 30 minutes.
2. Another assay which measures the stability in the absence of free calcium and where the pH is maintained at pH 6.2. This assay measures the decrease in calcium sensitivity: 10 micrograms of the variant were incubated under the following conditions: A 0.1 M acetate solution, pH adjusted to pH 6.2, containing 5% w/w common corn starch (free of calcium). Incubation was made in a water bath at 95° C. for 30 minutes.
3. A third assay wherein the conditions of assays nos. 1 and 2 have been combined. This assay measures the stability in the absence of calcium and at low pH (pH 5.5).
4. A fourth assay similar to no. 3. where the pH has been further reduced to pH 5.0.

Stability Determination

All the stability trials 1, 2, 3 and 4 have been made using the same set up. The method was:

The enzyme was incubated under the relevant conditions (1-4). Samples were taken at 0, 5, 10, 15 and 30 minutes and diluted 25 times (same dilution for all taken samples) in assay buffer (0.1 M 50 mM Britton buffer pH 7.3) and the activity was measured using the Phadebas assay (Pharmacia) under standard conditions pH 7.3, 37° C.

The activity measured before incubation (0 minutes) was used as reference (100%). The decline in percent was calculated as a function of the incubation time. The table shows the residual activity after 30 minutes of incubation.

Specific Activity Determination.

The specific activity was determined using the Phadebas assay (Pharmacia) as activity/mg enzyme. The activity was determined using the alpha-amylase assay described in the Materials and Methods section.

Results:

TABLE 8

Stability method no. 1./Low pH stability improvement

| Variant | Residual Activity after 30 minutes of incubation | Specific activity, 37° C., pH 7.3. Percent relative to Termamyl |
| --- | --- | --- |
| Termamyl wt. | 5% | 100% |
| H156Y | 15% | 100% |
| A209V | 18% | 100% |
| Q264S | 30% | 130% |
| H156Y + A181T + A209V | 39% | 100% |
| H133Y + H156Y + A181T + A209V + H293Y + A294V + G310D + H450Y | 58% | 85% |
| BAN/Termamyl hybrid* + H156Y + A181T + A209V | 48% | 115% |

TABLE 9

Stability method no. 2./decreased calcium sensitivity

| Variant | residual activity after 30 minutes of incubation | Specific activity, 37° C., pH 7.3. Percent relative to Termamyl |
| --- | --- | --- |
| Termamyl wt. | 52% | — |
| H156Y | 70% | — |
| A209V | 75% | — |
| A181T | 57% | 115% |
| N190F | 34% | 140% |
| N190F + N188P | 57% | 190% |

TABLE 10

Stability method no. 3. Low pH stability improvement + decreased calcium sensitivity

| Variant | Residual Activity after 30 minutes of incubation | Specific activity, 37° C., pH 7.3 Units/mg enzyme |
| --- | --- | --- |
| Termamyl wt. | 3% | — |
| BAN/Termamyl hybrid * + H156Y + A181T + A209V | 20% | — |
| Q264S | 5% | — |
| H140K + H142D | 5% | 115% |
| V128E | 50% ** | 115% |
| BAN/Termamyl hybrid * + H156Y + A181T + N190F + A209V | 39% | 170% |
| BAN/Termamyl hybrid * + H156Y + A181T + A209V + Q264S | 29% | 175% |
| BAN/Termamyl hybrid * + H156Y + A181T + N190F + A209V + Q264S | 57% | 210% |

* BAN (*B. amyloliquefaciens* alpha-amylase (SEQ ID NO: 4)/Termamyl (*B. licheniformis* alpha-amylase (SEQ ID NO: 2) PCR hybrid. First 33 N-terminal amino acids are BAN and the rest 36-483 are Termamyl (the construction of the variant is described in Example 1).
** Measured after 5 minutes of incubation. Compared to Termamyl wt. which under same conditions shows 36% residual activity.

TABLE 11

Stability method no. 4./Low pH stability improvement (pH 5.0) + decreased calcium sensitivity

| Variant | Residual Activity after 30 minutes of incubation | Specific activity, 37° C., pH 7.3 Units/mg enzyme |
| --- | --- | --- |
| BAN/Termamyl hybrid * + H156Y + A181T + N190F + A209V + Q264S | 9% | 210% |
| BAN/Termamyl hybrid * + H156Y + A181T + N190F + A209V + Q264S + E211Q | 28% | 160% |
| BAN/Termamyl hybrid * + H156Y + A181T + N190F + A209V + Q264S + H205C + D207Y + A210S | 33% | 130% |

* as indicated in relation to Table 10

The variants in the above Table 11 were constructed by means of the localized random mutagenesis described in Example 2.

Example 4

Alpha-Amylase Stability at Low pH and High Temperature

This example summarises the stability results of variants characterised by a fluorimetric assay at 70° C. under two different conditions, (1) pH 4.5 and 1 mM $CaCl_2$ and (2) pH 6.2 and 10 micro-M $CaCl_2$.

Description of Method

All fluorescence experiments were performed on a Perkin-Elmer LS-50 luminescence spectrometer using a 4-cuvette holder. The temperature was controlled by a circulating water-bath and measured directly in the cuvette using a Noronix Digital Thermometer (model NTD 100). During measurements, thorough mixing of reagents in the cuvette was ensured using magnetic stirrers operating at high stirring rate. The cuvettes were capped with teflon-lids to minimize evaporation.

Intrinsic protein-fluorescence (due to Trp side-chains) was monitored by excitation at 280 nm and emission at 350 nm. Slit-widths were 5 nm.

During kinetic measurements, 4 reactions were monitored in parallel. Data was collected in the Wavelength Programme dialogue, allowing automatic data-collection over a prolonged period (e.g., over an hour).

Unfolding was carried out at 70° C. Unfolding conditions were (1) 50 mM NaOAc pH 4.5 and 1 mM $CaCl_2$
(2) 50 mM NaOAc pH 6.2 and 10 micro-M $CaCl_2$.

Protein concentration was 5 micrograms/ml and glycerol was at 0.5% w/v (from protein stock solution).

Note: There was some variation from day to day in the absolute value of the unfolding half times due to slight temperature variations (occasioned by, e.g., different amounts of water in the water bath). However, Termamyl was always included as one of the four enzymes analyzed in each experiment, in effect making it an internal standard. Unfolding rates relative to this internal standard were satisfactorily reproducible (performed in triplicate).

Data analysis was carried out using GraphPad Prism software.

At pH 4.5, unfolding data could be fitted very satisfactorily to a single-exponential decay with drift:

$$F(t)=A^*\exp(-\ln(2)^*t/t_{1/2})+\text{drift}^*t+\text{offset} \quad (1)$$

where F is the measured fluorescence, A is the amplitude of the unfolding, t is time and $t_{1/2}$, is the half-time of unfolding.

At pH 6.2, unfolding was more complex (involving an initial lag phase), and data could not be fitted to eq. 1. Instead, the time taken for the fluorescence signal to decay to 50% of the initial signal was used as an apparent $t_{1/2}$.

From these half-times, the change in free energy of unfolding relative to that of Termamyl could be calculated as follows:

$$DDG=R^*T^*\ln(t_{1/2}^{mutant}/t_{1/2}^{Termamyl}) \quad (2)$$

where R is the universal gas constant and T is the temperature (the value of R*T is 0.5919, giving a DDG value in kcal/mol).

By converting data to DDG values, the destabilizing/stabilizing effects of different mutations can be compared directly and examined for additivity ($DDG_{1+2}=DDG_1+DDG_2$) and synergy ($DDG_{1+2}>DDG_1+DDG_2$) where $DDG_{1+2}$ is the energy-effect of introducing mutations 1 and 2.

Results

Unfolding of amylases at low pH and high temperature may be followed by the decay in Trp-fluorescence. At pH 4.5 and 1 mM CaCl$_2$, all amylases unfold fairly rapidly.

The unfolding data at pH 4.5 fit better to a double-exponential equation than to a single-exponential equation. However, since the second phase is very slow, it is approximated by a linear drift (equation 1). Unfolding at pH 6.2 and 10 micro-M CaCl$_2$ at 70° C. is much less rapid than at pH 4.5 despite the low [Ca$^{2+}$]. Unfolding is far from complete within an hour and it is not possible to fit the data to a single-exponential equation. Instead, the time taken for the fluorescence signal to decay to 50% of the initial signal is used as an apparent $t_{1/2}$.

Results of the fluorescence assay are presented in Table 12.

TABLE 12

Summary of data for unfolding of Termamyl variants pH 4.5 and pH 6.2 at 70° C.
At pH 4.5, $t_{1/2}^{Termamyl}$ = 200 s; at pH 6.2, $t_{1/2}^{Termamyl}$ = 2800 s.
DDG = $-RT*\ln(t_{1/2}^{Termamyl}/t_{1/2}^{mutant})$

| | pH 4.5, 1 mM CaCl$_2$ | | pH 6.2, 10 microM CaCl$_2$ | |
| --- | --- | --- | --- | --- |
| Mutation | DDG (kcal/mol) | $t_{1/2}/t_{1/2}^{Termamyl}$ | DDG (kcal/mol) | $t_{1/2}/t_{1/2}^{Termamyl}$ |
| Wildtype | 0 | 1.0 | 0 | 1.0 |
| A209V | −0.36 | 1.85 | −0.72 | 3.39 |
| H133Y + A209V | −0.77 | 3.67 | −0.61 | 2.78 |
| H156Y | 0.06 | 0.90 | −0.10 | 1.18 |
| A181T | −0.06 | 1.10 | −0.28 | 1.60 |
| A181T + A209V | −0.44 | 2.09 | <−1 (73%)[a] | >5 |
| S187D | 0.37 | 0.54 | 0.19 | 0.72 |
| H450Y | −0.49 | 2.29 | 0.15 | 0.78 |
| L270D | −0.35 | 1.8 | −0.10 | 1.2 |
| H156Y + A181T | −0.17 | 1.34 | −0.62 | 2.84 |
| H133I | −0.33 | 1.75 | −0.42 | 2.02 |
| H133Y + H156Y + A181T + A209V + H293Y + A294V + G310D + H450Y | −0.96 | 5.10 | <−1 (58%)[a] | >5 |
| V128E | −0.10 | 1.2 | −0.25 | 1.5 |
| H156Y + A181T + A209V | −0.32 | 1.71 | −0.49 | 2.30 |
| H156Y + A181T + A209V + H450Y | −0.42 | 2.05 | −0.63 | 2.92 |
| H133I + H156Y + A181T + A209V + H450Y | −0.81 | 3.9 | <−1 (65%)[a] | >5 |
| H133I + H156Y + A181T + A209V | −0.70 | 3.3 | <−1 (77%)[a] | >5 |
| Q264S | −0.26 | 1.6 | −0.14 | 1.3 |
| Delta(1, 2) + L3V + M15T + R23K + S31A + A32E + Y33H + A35S + E36D + H37I + H156Y + A181T + A209V | −0.43 | 2.1 | −0.82 | 4.0 |
| Q264S + N265Y | −0.33 | 1.8 | −0.07 | 1.1 |
| N190F + Q264S + N265Y | −1.07 | 6.1 | −0.67 | 3.1 |
| N190F + H133I + A209V + Q264S + N265Y | −1.66 | 16.5 | <−1 (82%)[a] | >5 |
| Delta(1, 2) + L3V + M15T + R23K + S31A + A32E + Y33H + A35S + E36D + H37I + H156Y + A181T + N190F + A209V | −0.30 | 1.7 | <−1 (66%)[a] | >5 |
| Delta(1, 2) + L3V + M15T + R23K + S31A + A32E + Y33H + A35S + E36D + H37I + H156Y + A181T + A209V + Q264S | −0.43 | 2.1 | −0.86 | 4.3 |
| Delta(1, 2) + L3V + M15T + R23K + S31A + A32E + Y33H + A35S + E36D + H37I + H156Y + A181T + N190F + A209V + Q264S | −0.36 | 1.8 | <−1 (76%)[a] | >5 |
| H156Y + A181T + N190F + A209V + Q264S | −1.3 | 8.6 | <−1 (66%)[a] | >5 |

[a]The percentage indicates the level to which the initial fluorescence level had declined in the course of 3 hours at 70° C. The slow decline is indicative of high stability.

Example 5

Alpha-Amylase Variants with Increased Specific Activity

This example summarizes the results of variants characterised by having increased specific activity compared to Termamyl wt. The presence of these substitutions either in combination with each other or as single substitutions added to stabilizing substitutions increases the specific activity of the resulting variant. The specific activity was determined using the alpha-amylase (Phadebas) assay described in the Materials and Methods where the activity/mg enzyme was determined. The activity was determined using the following description where the pH was 7.3, temperature 37° C. and testing time 15 minutes and buffer as defined.

| MUTATION | Specific Activity (Phadebas Assay), Index Relative to TERMAMYL WT. |
|---|---|
| S187D | 260% |
| V54I | 160% |
| BAN/Termamyl hybrid: | 140% |
| (Δ(1, 2) + L3V + M15T + R23K + S31A + A32E + Y33H + A35S + E36D + H37I) | |
| Δ(D372 + S373 + Q374) | 125% |
| Δ(K370 + G371 + D372) | 125% |
| BAN/Termamyl hybrid: | 360% |
| (Δ(1, 2) + L3V + M15T + R23K + S31A + A32E + Y33H + A35S + E36D + H37I + V54I + S187D + Δ(D372 + S373 + Q374) | |
| Q264S | 130% |
| Y290E | 155% |
| Y290K | 140% |
| N190F | 150% |

Example 6

Testing of Specificity Variants (Saccharification)

It has been reported previously (U.S. Pat. No. 5,234,823) that, when saccharifying with glucoamylase and pullulanase, the presence of residual alpha-amylase activity arising from the liquefaction process, can lead to lower yields of glucose, if the alpha-amylase is not inactivated before the saccharification stage. This inactivation can be typically carried out by adjusting the pH to below 4.3 at 95° C., before lowering the temperature to 60° C. for saccharification.

The reason for this negative effect on glucose yield is not fully understood, but it is assumed that the liquefying alpha-amylase (for example Termamyl 120 L from *B. licheniformis*) generates "limit dextrins" (which are poor substrates for pullulanase), by hydrolyzing 1,4-alpha-glucosidic linkages close to and on both sides of the branching points in amylopectin. Hydrolysis of these limit dextrins by glucoamylase leads to a build up of the trisaccharide panose, which is only slowly hydrolyzed by glucoamylase.

The development of a thermostable alpha-amylase, which does not suffer from this disadvantage would be a significant improvement, as no separate inactivation step would be required.

A number of *B. licheniformis* alpha-amylase variants, with altered specificity, were evaluated by saccharifying a DE 10 Maltodextrin substrate with *A. niger* glucoamylase and *B. acidopullulyticus* pullulanase under conditions where the variant amylase was active.

The saccharification reactions were monitored by taking samples at 24 hour intervals and analysing them by HPLC. The standard reaction conditions were:

| | |
|---|---|
| Substrate concentration | 28.2% w/w |
| Temperature | 60° C. |
| Initial pH (at 60° C.) | 4.7 |
| Enzyme dosage | |
| Glucoamylase | 0.18 AG/g DS |
| Pullulanase | 0.06 PUN/g DS |
| alpha-amylase | 60 NU/g DS |

The following enzymes were used:
Glucoamylase: AMG (Novo Nordisk) 153 AG/g
Pullulanase: Promozyme (Novo Nordisk) 295 PUN/g
Alpha-amylase:

| | |
|---|---|
| Termamyl (Novo Nordisk) | 135 KNU/g |
| V54Y | 313 KNU/g |
| A52W | 5,116 NU/ml |
| D53E | 3,280 NU/ml |
| D53W | 599 NU/ml |
| A52W + V54Y | 134 NU/ml |

The mutations listed in the alpha-amylase list above are used to indicate variants of the *B. licheniformis* alpha-amylase (SEQ ID NO: 2) (Termamyl) which has been modified by the indicated mutation(s).

Substrates for saccharification were prepared by dissolving 230 g DE 10 spray-dried maltodextrin, prepared from common corn starch, in 460 ml boiling deionized water and adjusting the dry substance to approximately 30% w/w. The pH was adjusted to 4.7 (measured at 60° C.) and aliquots of substrate corresponding to 15 g dry weight, were transferred to 50 ml blue cap glass flasks.

The flasks were then placed in a shaking water bath equilibrated at 60° C., and the to enzymes added. The pH was readjusted to 4.7 where necessary. 2 ml samples were taken periodically, the pH adjusted to about 3.0, and then heated in a boiling water bath for 15 minutes to inactivate the enzymes. After cooling, the samples were treated with approximately 0.1 g mixed bed ion exchange resin (BIO-Rad 501 X8 (D)) for 30 minutes on a rotary mixer to remove salts and soluble N. After filtration, the carbohydrate composition was determined by HPLC. After 72 hours, the following results were obtained:

| Added alpha-amylase | % $DP_1$ | % $DP_2$ | % $DP_3$ | % $DP_{4+}$ |
|---|---|---|---|---|
| None (control) | 96.59 | 2.2 | 0.3 | 1.0 |
| V54Y | 96.5 | 2.2 | 0.4 | 0.9 |
| A52W + V54Y | 96.4 | 2.2 | 0.5 | 0.9 |
| Termamyl | 96.3 | 2.1 | 0.8 | 0.8 |

Compared with the control (no active alpha-amylase present during liquefaction), the presence of active alpha-amylase variants V54Y and A52W+V54Y did not lead to elevated panose levels ($DP_3$).

If these alpha-amylase variants are used for starch liquefaction, it will not be necessary to inactivate the enzyme before the commencement of saccharification.

Example 7

Evaluation of B. licheniformis Variants Under Simulated Liquefaction Conditions The standard process for industrial starch liquefaction comprises two stages, normally referred to as primary and secondary liquefaction. In the first stage, a 30-40% w/w starch slurry at pH 5.5-6.0, to which has been added a thermostable alpha-amylase from *B. licheniformis* or *B. stearothermophillus*, is heated to 105-110° C. in a jet cooker where live steam is injected into the starch stream. After a holding time of 5-10 minutes under pressure at this temperature, the liquefied starch is flash cooled to about 95° C. and held at that temperature for 60-120 minutes.

In order to evaluate small quantities of enzyme on a laboratory scale the following test method was used:

10 g aliquots of a suspension of common corn starch (Cerestar GL 3406) in deionized water (approx. 30% w/w) are weighed out into 100 ml conical flasks (Schott GL 125) which are fitted with tight fitting screw caps. The pH, calcium level and enzyme dosage in the suspension can be varied.

4 flasks are used for each different set of experimental conditions. The flasks are placed in a shaking oil-bath (Heto VS 01) maintained at 105° C. After a period of 7 minutes, cold oil is poured into the bath to lower the temperature to 95° C. For each experimental series, flasks are removed after 20, 40, 60 and 90 minutes and immediately cooled under running water. One drop of 1 N HCL is added to each flask to inactivate the enzyme. The reaction is monitored by measuring the DE (reducing sugar content expressed as glucose) using the Neocuproine method.

The details of this method can be found in "Determination of reducing sugar with improved precision. Dygert et al., 1965, *Anal. Biochem.* 13: 368. The following DEs were recorded after 90 minutes:

| pH 5.5, 5 ppm calcium added, 10.9 mg enzyme protein/g starch | | | |
|---|---|---|---|
| I.D. no. | Hybrid + H156Y + A181T + N190F + A209V + Q264S | Hybrid + H156Y + A181T + N190F + A209V | H156Y + A181T + N190F + A209V + Q264S |
| 001-97 | 14.8 | 15.2 | 12.6 |

REFERENCES CITED

Klein et al., 1992, *Biochemistry* 31: 8740-8746,
Mizuno et al., 1993, *J. Mol. Biol.* 234: 1282-1283,
Chang et al., 1993, *J. Mol. Biol.* 229: 235-238,
Larson, 1994, *J. Mol. Biol.* 235: 1560-1584,
Lawson, 1994, *J. Mol. Biol.* 236: 590-600,
Qian et al., 1993, *J. Mol. Biol.* 231: 785-799,
Brady et al., *Acta Crystallogr. sect. B* 47: 527-535,
Swift et al., *Acta Crystallogr. sect. B* 47: 535-544
A. Kadziola, Ph.D. Thesis: "An alpha-amylase from Barley and its Complex with a Substrate Analogue Inhibitor Studied by X-ray Crystallography", Department of Chemistry University of Copenhagen 1993
MacGregor, 1987, *Food Hydrocolloids* 1(5-6):
Diderichsen and Christiansen, 1988, "Cloning of a maltogenic alpha-amylase from *Bacillus stearothermophilus*", *FEMS Microbiol. Letters* 56: 53-60
Hudson et al., Practical Immunology, Third edition (1989), Blackwell Scientific Publications,
Sambrook et al., *Molecular Cloning: A Laboratory Manual*, 2nd Ed., Cold Spring Harbor, 1989
Beaucage and Caruthers, 1981, *Tetrahedron Letters* 22: 1859-1869
Matthes et al., 1984, *The EMBO J.* 3: 801-805.
Saiki et al., 1988, *Science* 239: 487-491.
Morinaga et al., 1984, *Biotechnology* 2: 646-639

| pH 6.0, 5 ppm calcium added, 10.9 mg enzyme protein/g starch | | | | | | | | | |
|---|---|---|---|---|---|---|---|---|---|
| I.D. no. | Termamyl | Hybrid + H156Y + A181T + N190F + A209V + Q264S | Hybrid + H156Y + A181T + N190F + A209V | Hybrid + H156Y + A181T + N190F + A209V + Q264S | Hybrid + H156Y + A181T + N190F + A209V + Q264S | Hybrid + H156Y + A181T + A209V | Q264S | Q264S + N265Y | N190F + Q264S + N265Y | H156Y + A181T + A209V |
| 045-96 |  | 16.0 | 16.9 | 13.2 |  |  |  |  |  |
| 038-96 | 6.5 | 13.9 |  |  |  |  |  |  |  |
| 035-96 |  |  | 15.2 |  | 12.9 | 9.9 |  |  |  |
| 033-96 |  |  |  |  |  |  | 6.7 | 7.2 | 12.1 |
| 031-96 | 4.5 |  |  |  |  |  | 7.0 | 8.8 | 12.5 |
| 029-96 | 4.0 |  |  |  |  | 8.7 | 5.2 |  |  | 7.7 |
| 039-96 |  | 14.9 | 16.3 |  | 14.4 |  |  |  |  |

Hybrid=BAN/Termamyl PCR hybrid as described in Example 3

| pH 6.0, 40 ppm calcium added, 10.9 mg enzyme protein/g starch | |
|---|---|
| I.D. no. | Termamyl |
| 045-96 | 12.6 |
| 007-97 | 12.1 |

Nelson and Long, 1989, *Analytical Biochemistry* 180: 147-151
Hunkapiller et al., 1984, *Nature* 310: 105-111
Higuchi et al., 1988, "A general method of in vitro preparation and specific mutagenesis of DNA fragments: study of protein and DNA interactions", *Nucl. Acids Res.* 16: 7351-7367.
Dubnau et al., 1971, *J. Mol. Biol.* 56: 209-221.
Gryczan et al., 1978, *J. Bacteriol.* 134: 318-329.
S. D. Erlich, 1977, *Proc. Natl. Acad. Sci.* 74: 1680-1682.
Boel et al., 1990, *Biochemistry* 29: 6244-6249.

The invention claimed is:

1. A variant of a parent alpha-amylase, which variant has alpha-amylase activity and has at least 95% homology with SEQ ID NO: 2, 4, 6, 38, 39 or 40, and comprises one or more mutations selected from the group consisting of S334A,V,T,L,I,D; L335G,A,S,T,N; E336R+R375E; T337D,K; T338D,E; T339D; Q360K,R,E; D365N; and G371D,R, wherein the mutations correspond to SEQ ID NO:2.

2. The variant of claim 1, wherein the parent alpha-amylase is selected from the group consisting of:
   a B. licheniformis alpha-amylase,
   a B. amyloliquefaciens alpha-amylase,
   a B. stearothermophilus alpha-amylase,
   an alpha-amylase having the sequence shown in SEQ ID NO:38,
   an alpha-amylase having the sequence shown in SEQ ID NO:39, and
   an alpha-amylase having the sequence shown in SEQ ID NO:40.

3. A detergent additive comprising an alpha-amylase variant of claim 1 and a surfactant.

4. A composition comprising:
   (a) a mixture of an alpha-amylase from B. licheniformis with one or more variants of claim 1 derived from (as the parent alpha-amylase) a B. stearothermophilus alpha-amylase; or
   (b) a mixture of an alpha-amylase from B. stearothermophilus with one or more variants of claim 1; or
   (c) a mixture of one or more variants of claim 1 derived from (as the parent alpha-amylase) the B. stearothermophilus alpha-amylase with one or more variants according to the invention derived from one or more other parent alpha-amylases.

5. A method for processing starch, comprising treating the starch with a variant of claim 1.

6. A starch liquefaction process comprising treating starch with a variant of claim 1.

7. A DNA construct comprising a DNA sequence encoding a variant of claim 1.

8. A recombinant expression vector which carries a DNA construct of claim 7.

9. A cell which is transformed with a DNA construct of claim 7.

10. The cell of claim 9, which is a microorganism.

11. The cell of claim 10, which is a bacterium or a fungus.

12. The cell of claim 11, which is a gram-positive bacterium such as *Bacillus alkalophilus, Bacillus amyloliquefaciens, Bacillus brevis, Bacillus coagulans, Bacillus circulans, Bacillus lautus, Bacillus licheniformis, Bacillus lentus, Bacillus stearothermophilus, Bacillus subtilis*, or *Bacillus thuringiensis*.

13. The variant of claim 1, wherein the variant has at least 95% homology to SEQ ID NO: 2.

14. The variant of claim 1, wherein the variant has at least 95% homology to SEQ ID NO: 4.

15. The variant of claim 1, wherein the variant has at least 95% homology to SEQ ID NO: 6.

16. The variant of claim 1, wherein the variant has at least 95% homology to SEQ ID NO: 38.

17. The variant of claim 1, wherein the variant has at least 95% homology to SEQ ID NO: 39.

18. The variant of claim 1, wherein the variant has at least 95% homology to SEQ ID NO: 40.

* * * * *